United States Patent
Irisawa et al.

(10) Patent No.: US 11,649,334 B2
(45) Date of Patent: May 16, 2023

(54) WATER-SOLUBLE COMPOSITION, PRODUCTION METHOD FOR CURED PRODUCT THEREOF, AND CURED PRODUCT THEREOF, AND ACYL PHOSPHINATE

(71) Applicant: ADEKA CORPORATION, Tokyo (JP)

(72) Inventors: Masatomi Irisawa, Tokyo (JP); Kenji Hara, Tokyo (JP)

(73) Assignee: ADEKA CORPORATION, Tokyo (JP)

(*) Notice: Subject to any disclaimer, the term of this patent is extended or adjusted under 35 U.S.C. 154(b) by 762 days.

(21) Appl. No.: 16/493,865

(22) PCT Filed: Mar. 13, 2018

(86) PCT No.: PCT/JP2018/009786
§ 371 (c)(1),
(2) Date: Sep. 13, 2019

(87) PCT Pub. No.: WO2018/168870
PCT Pub. Date: Sep. 20, 2018

(65) Prior Publication Data
US 2020/0032021 A1    Jan. 30, 2020

(30) Foreign Application Priority Data
Mar. 15, 2017 (JP) .............................. JP2017-049792

(51) Int. Cl.
*C08J 7/18* (2006.01)
*C08F 2/50* (2006.01)
(Continued)

(52) U.S. Cl.
CPC ............... *C08J 7/18* (2013.01); *C07C 215/40* (2013.01); *C07D 211/46* (2013.01);
(Continued)

(58) Field of Classification Search
CPC ........ C08J 7/18; C07C 215/40; C07D 211/46; C07D 295/037; C07D 207/04; C07D 265/30; C07F 9/304; C07F 9/307; C09D 4/06; C09D 11/101; C09J 4/06; C08F 2/48; C08F 299/025; C08F 20/56; C08F 2/44;
(Continued)

(56) References Cited

U.S. PATENT DOCUMENTS 4,719,297 A * 1/1988 Henne .................. G03F 7/029 987/153
5,891,972 A    4/1999 Egra et al.
(Continued)

FOREIGN PATENT DOCUMENTS

CN    104350422 A    2/2015
CN    105377999 A    3/2016
(Continued)

OTHER PUBLICATIONS

Extended European Search Report for European Application No. 18767661.4, dated Aug. 6, 2020.
Fairbanks et al., "Photoinitiated polymerization of PEG-diacrylate with lithium phenyl-2,4,6-trimethylbenzoylphosphinate: polyermization rate and cytocompatibility," Biomaterials, vol. 30, 2009 (published online Sep. 23, 2009, pp. 6702-6707.
Ta-Shma et al., "A kinetic study of competing fragmentation and hydrolyses of phenyl hydrogen α-hydroxyiminobenzylphosphonate—a case of acid mediated inhibition of acid catalysis," J. Chem. Soc., Perkin Trans., vol. 2, 2001, pp. 1404-1407.
Tong et al., "Visible Light Mediated Fast Iterative RAFT Synthesis of Amino-Based Reactive Copolymers in Water at 20° C.," Macromol. Rapid Commun., vol. 34, 2013, pp. 1827-1832.
(Continued)

*Primary Examiner* — Jessica M Roswell
(74) *Attorney, Agent, or Firm* — Birch, Stewart, Kolasch & Birch, LLP

(57) ABSTRACT

Provided are: a water-soluble composition which has excellent storage stability and is adaptable to a wide range of light sources and capable of forming a highly fine pattern; a method of producing a cured product of the same; a cured product of the same; and an acylphosphinate. The water-soluble composition contains: an acylphosphinate (A) represented by Formula (I) below, wherein $X^1$ represents an aryl group having 6 to 15 carbon atoms; $X^2$ represents a linear alkyl group having 1 to 8 carbon atoms or the like; $A^{m+}$ represents an alkali metal ion or the like; and m represents a number of 1 to 3; and a compound (B) having a group represented by Formula (II) below, wherein $R^1$ represents a hydrogen atom or the like; $Z^1$ represents an oxygen atom or the like; $R^2$ represents a hydrogen atom or the like; $Z^2$ represents an alkylene group having 1 to 6 carbon atoms; n represents a number of 0 to 30; * means a bond; and, when the compound (B) has plural groups represented by Formula (II), plural $R^1$'s, $Z^1$'s, $Z^2$'s and n's are each optionally the same or different.

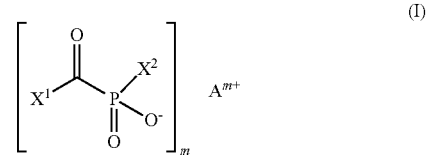

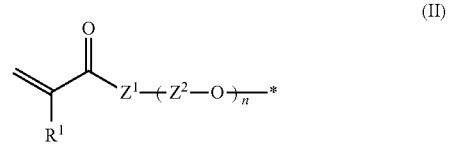

12 Claims, No Drawings

(51) Int. Cl.
  *C07C 215/40*      (2006.01)
  *C09D 4/06*        (2006.01)
  *C07D 211/46*      (2006.01)
  *C07D 295/037*     (2006.01)
  *C07F 9/30*        (2006.01)
  *C09D 11/101*      (2014.01)
  *C09J 4/06*        (2006.01)
  *G03F 7/029*       (2006.01)

(52) U.S. Cl.
  CPC .......... *C07D 295/037* (2013.01); *C07F 9/304* (2013.01); *C09D 4/06* (2013.01); *C09D 11/101* (2013.01); *C09J 4/06* (2013.01); *G03F 7/029* (2013.01)

(58) Field of Classification Search
  CPC .. C08F 2/50; C08F 20/28; C08F 20/58; C08F 20/60; C08K 5/5313
  See application file for complete search history.

(56) References Cited

U.S. PATENT DOCUMENTS

| | | |
|---|---|---|
| 2006/0004116 A1 | 1/2006 | Kishi et al. |
| 2006/0249269 A1 | 11/2006 | Kurian et al. |
| 2010/0015360 A1 | 1/2010 | Kyota |
| 2011/0104453 A1 | 5/2011 | Shinjo et al. |
| 2015/0037588 A1 | 2/2015 | Kato |
| 2015/0159032 A1 | 6/2015 | Yofu |

FOREIGN PATENT DOCUMENTS

| | | |
|---|---|---|
| EP | 0 819 704 A1 | 1/1998 |
| JP | 57-197289 A | 12/1982 |
| JP | 2000-159621 A | 6/2000 |
| JP | 2005-307199 A | 11/2005 |
| JP | 2007-277380 A | 10/2007 |
| JP | 2010-24276 A | 2/2010 |
| JP | 2011-116946 A | 6/2011 |
| JP | 2012-7070 A | 1/2012 |
| TW | 201339189 A | 10/2013 |
| WO | WO 2014/050551 A1 | 4/2014 |
| WO | WO 2014/209124 A1 | 12/2014 |
| WO | WO 2015/010016 A1 | 1/2015 |

OTHER PUBLICATIONS

Chinese Office Action, dated Jun. 9, 2021, for Chinese Application No. 201880014240.3.
International Search Report, issued in PCT/JP2018/009786, dated Jun. 12, 2018.
Written Opinion of the International Searching Authority, issued in PCT/JP2018/009786, dated Jun. 12, 2018.
Taiwanese Office Action and Search Report for Taiwanese Application No. 107108779, dated Jul. 7, 2021.

* cited by examiner

WATER-SOLUBLE COMPOSITION, PRODUCTION METHOD FOR CURED PRODUCT THEREOF, AND CURED PRODUCT THEREOF, AND ACYL PHOSPHINATE

TECHNICAL FIELD

The present invention relates to: a water-soluble composition; a method of producing a cured product of the same; a cured product of the same; and an acylphosphinate. More particularly, the present invention relates to: a water-soluble composition which has excellent storage stability and is adaptable to a wide range of light sources and capable of forming a highly fine pattern; a method of producing a cured product of the same; a cured product of the same; and an acylphosphinate.

BACKGROUND ART

Water-soluble compositions are used in a variety of applications, such as paints, inks, adhesives, and optical films. Focusing attention on water-soluble initiators of water-soluble compositions, Patent Document 1 proposes a water-soluble ink composition which contains fine particles, an ethylenically unsaturated group-containing polymerizable compound, a photopolymerization initiator having a betaine structure, and water; Patent Document 2 proposes an ink composition having good temporal stability, curing stability and landing position accuracy, which ink composition contains α-aminoacetophenone having a morpholine structure as a water-soluble initiator and a compound having an acrylamide structure as a water-soluble compound; and Patent Document 3 proposes a dental adhesive composition having excellent adhesiveness to tooth substances, particularly dentin, which composition contains an acrylate-based monomer along with a water-soluble acylphosphine oxide compound as a photopolymerization initiator.

RELATED ART DOCUMENTS

Patent Documents

[Patent Document 1] WO2014/050551A
[Patent Document 2] JP2012-007070A
[Patent Document 3] JP2000-159621A

SUMMARY OF THE INVENTION

Problems to be Solved by the Invention

Water-soluble compositions are required to have excellent storage stability and be adaptable to a wide range of light sources and capable of forming a highly fine pattern. Under this circumstance, the water-soluble compositions proposed in Patent Documents 1 to 3 cannot necessarily satisfy these properties at such a high level that is demanded by the market, and a further improvement is desired in water-soluble compositions at present.

In view of the above, an object of the present invention is to provide: a water-soluble composition which has excellent storage stability and is adaptable to a wide range of light sources and capable of forming a highly fine pattern; a method of producing a cured product of the same; a cured product of the same; and an acylphosphinate.

Means for Solving the Problems

The present inventors intensively studied to solve the above-described problems and consequently discovered that the problems can be solved by using a water-soluble composition that contains an acylphosphinate having a specific structure and an alkylene oxide-modified (meth)acrylate compound or a (meth)acrylamide compound, thereby completing the present invention.

That is, a water-soluble composition of the present invention is characterized by comprising:

an acylphosphinate (A) represented by the following Formula (I):

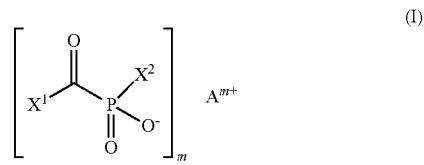

wherein, $X^1$ represents an aryl group having 6 to 15 carbon atoms;

hydrogen atoms in the group represented by $X^1$ are each optionally substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, or a branched halogenated alkoxy group having 3 to 8 carbon atoms;

$X^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or an aryl group having 6 to 15 carbon atoms;

hydrogen atoms in the aryl group having 6 to 15 carbon atoms that is represented by $X^2$ are each optionally substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, a branched halogenated alkoxy group having 3 to 8 carbon atoms, a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group;

a methylene group in the group represented by $X^2$ is optionally substituted with an oxygen atom or a sulfur atom;

$A^{m+}$ represents an alkali metal ion, an alkaline earth metal ion, or $N^+HY^1Y^2Y^3$;

$Y^1$, $Y^2$ and $Y^3$ each independently represent a hydrogen atom, a hydroxy group, an alkyl group having 1 to 6 carbon atoms, an alkenyl group having 1 to 6 carbon atoms, an aryl group having 6 to 15 carbon atoms, or an arylalkyl group having 7 to 13 carbon atoms;

hydrogen atoms in the groups represented by $Y^1$, $Y^2$ and $Y^3$ are each optionally substituted with a hydroxy group;

methylene groups in the groups represented by $Y^1$, $Y^2$ and $Y^3$ are each optionally substituted with an oxygen atom, a sulfur atom, a carbonyl group, or $—N^+H—$;

one or more combinations of $Y^1$ and $Y^2$, $Y^1$ and $Y^3$, and $Y^2$ and $Y^3$ are optionally bound with each other to form a ring; and m represents a number of 1 to 3; and a compound (B) having a group represented by the following Formula (II):

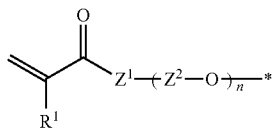

wherein, $R^1$ represents a hydrogen atom or a methyl group;

$Z^1$ represents an oxygen atom or —$NR^2$—;

$R^2$ represents a hydrogen atom or a hydrocarbon group having 1 to 20 carbon atoms;

$Z^2$ represents an alkylene group having 1 to 6 carbon atoms;

n represents a number of 0 to 30;

* means a bond; and when the compound (B) has plural groups represented by Formula (II), plural $R^1$'s, $Z^1$'s, $Z^2$'s and n's are each optionally the same or different.

In the water-soluble composition of the present invention, it is preferred that $X^1$ in the above-described Formula (I) be a 2,4,6-trimethylphenyl group. In the water-soluble composition of the present invention, it is also preferred that $X^2$ and $A^{m+}$ in the above-described Formula (I) be a phenyl group and $N^+HY^1Y^2Y^3$, respectively. Further, in the water-soluble composition of the present invention, it is preferred that $A^{m+}$ in the above-described Formula (I) be $N^+HY^1Y^2Y^3$, and at least one hydrogen atom of $Y^1$, $Y^2$ and $Y^3$ be substituted with a hydroxy group. Still further, in the water-soluble composition of the present invention, it is preferred that $Z^1$ in the above-described Formula (II) be —$NR^2$—. Yet still further, it is preferred that the water-soluble composition of the present invention further contain a coloring agent (C).

A method of producing a cured product according to the present invention is characterized by comprising curing the water-soluble composition of the present invention by irradiation with light or heating.

Further, a cured product of the present invention is characterized by being obtained from the water-soluble composition of the present invention.

Still further, the acylphosphinate of the present invention is an acylphosphinate represented by the following Formula (I):

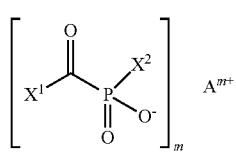

wherein, $X^1$ represents an aryl group having 6 to 15 carbon atoms;

hydrogen atoms in the group represented by $X^1$ are each optionally substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, or a branched halogenated alkoxy group having 3 to 8 carbon atoms;

$X^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or an aryl group having 6 to 15 carbon atoms;

hydrogen atoms in the aryl group having 6 to 15 carbon atoms that is represented by $X^2$ are each optionally substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, a branched halogenated alkoxy group having 3 to 8 carbon atoms, a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group;

a methylene group in the group represented by $X^2$ is optionally substituted with an oxygen atom or a sulfur atom;

$A^{m+}$ represents an alkali metal ion, an alkaline earth metal ion, or $N^+HY^1Y^2Y^3$;

$Y^1$, $Y^2$ and $Y^3$ each independently represent a hydrogen atom, a hydroxy group, an alkyl group having 1 to 6 carbon atoms, an alkenyl group having 1 to 6 carbon atoms, an aryl group having 6 to 15 carbon atoms, or an arylalkyl group having 7 to 13 carbon atoms;

hydrogen atoms in the groups represented by $Y^1$, $Y^2$ and $Y^3$ are each optionally substituted with a hydroxy group;

methylene groups in the groups represented by $Y^1$, $Y^2$ and $Y^3$ are each optionally substituted with an oxygen atom, a sulfur atom, a carbonyl group, or —$N^+H$—;

one or more combinations of $Y^1$ and $Y^2$, $Y^1$ and $Y^3$, and $Y^2$ and $Y^3$ are optionally bound with each other to form a ring; and m represents a number of 1 to 3, the acylphosphinate being characterized in that:

in the above-described Formula (I), $X^2$ is a phenyl group and $A^{m+}$ is $N+HY^1Y^2Y^3$, and one or more combinations of $Y^1$ and $Y^2$, $Y^1$ and $Y^3$, and $Y^2$ and $Y^3$ are bound with each other to form a ring.

In the acylphosphinate of the present invention, it is preferred that $A^{m+}$ in Formula (I) be $N^+HY^1Y^2Y^3$ and at least one hydrogen atom of $Y^1$, $Y^2$ and $Y^3$ be substituted with a hydroxy group.

Effects of the Invention

According to the present invention, a water-soluble composition which has excellent storage stability and is adaptable to a wide range of light sources and capable of forming a highly fine pattern, a method of producing a cured product of the same, a cured product of the same, and an acylphosphinate can be provided. The water-soluble composition of the present invention can yield a highly fine pattern with light of various wavelengths corresponding to high-pressure mercury lamps, ultra high-pressure mercury lamps, electrodeless lamps, LED light sources and the like. In addition, since this composition has excellent storage stability, it can be preferably used in a variety of applications, such as paints, inks, adhesives, and optical films. Moreover, the acylphosphinate of the present invention can be preferably used in the water-soluble composition of the present invention.

MODE FOR CARRYING OUT THE INVENTION

The water-soluble composition of the present invention will now be described. The water-soluble composition of the present invention contains an acylphosphinate (A) represented by Formula (I) below and a compound (B) having a group represented by Formula (II) below. The water-soluble composition of the present invention not only has excellent storage stability and can exist by itself as a liquid but also is adaptable to light sources of various wavelengths; therefore, a cured product can be easily and simply produced therefrom. The components are described below in the order mentioned.

<Acylphosphinate (A)>

The acylphosphinate (A) according to the water-soluble composition of the present invention is not particularly restricted as long as it is the acylphosphinate of the present invention and contains a group represented by the following Formula (I):

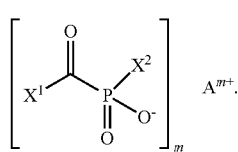

In Formula (I), $X^1$ represents an aryl group having 6 to 15 carbon atoms, and hydrogen atoms in the group represented by $X^1$ are each optionally substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, or a branched halogenated alkoxy group having 3 to 8 carbon atoms.

Further, in Formula (I), $X^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or an aryl group having 6 to 15 carbon atoms.

Hydrogen atoms in the aryl group having 6 to 15 carbon atoms that is represented by $X^2$ are each optionally substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, a branched halogenated alkoxy group having 3 to 8 carbon atoms, a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group, and a methylene group in the group represented by $X^2$ is optionally substituted with an oxygen atom or a sulfur atom.

$A^{m+}$ represents an alkali metal ion, an alkaline earth metal ion, or $N^+HY^1Y^2Y^3$, and $Y^1$, $Y^2$ and $Y^3$ each independently represent an alkyl group having 1 to 6 carbon atoms, an alkenyl group having 1 to 6 carbon atoms, an aryl group having 6 to 15 carbon atoms, or an arylalkyl group having 7 to 13 carbon atoms. Moreover, hydrogen atoms in the groups represented by $Y^1$, $Y^2$ and $Y^3$ are each optionally substituted with a hydroxy group; methylene groups in the groups represented by $Y^1$, $Y^2$ and $Y^3$ are each optionally substituted with an oxygen atom, a sulfur atom, a carbonyl group, or $-N^+H-$; one or more combinations of $Y^1$ and $Y^2$, $Y^1$ and $Y^3$, and $Y^2$ and $Y^3$ are optionally bound with each other to form a ring; and m represents a number of 1 to 3.

Examples of the aryl group having 6 to 15 carbon atoms that is represented by $X^1$, $X^2$ and $Y^1$ to $Y^3$ in Formula (I) include phenyl, trimethylphenyl, tolyl, xylyl, 2,4,6-trimethylphenyl, naphthyl, and an anthryl group.

Examples of a group optionally substituting the hydrogen atoms in the groups represented by $X^1$ and $X^2$ in Formula (I) include a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, and a branched halogenated alkoxy group having 3 to 8 carbon atoms. Examples of the halogen atom include a fluorine atom, a chlorine atom, a bromine atom, and an iodine atom.

Examples of the linear alkyl group having 1 to 8 carbon atoms include methyl, ethyl, propyl, butyl, amyl, hexyl, heptyl, and octyl.

Examples of the branched alkyl group having 3 to 8 carbon atoms include isopropyl, butyl, isobutyl, s-butyl, t-butyl, isoamyl, t-amyl, isooctyl, 2-ethylhexyl, and t-octyl.

The linear halogenated alkyl group having 1 to 8 carbon atoms represents any of the above-described linear alkyl groups having 1 to 8 carbon atoms in which at least one hydrogen atom is substituted with a halogen atom.

The branched halogenated alkyl group having 3 to 8 carbon atoms represents any of the above-described branched alkyl groups having 3 to 8 carbon atoms in which at least one hydrogen atom is substituted with a halogen atom.

Examples of the linear alkoxy group having 1 to 8 carbon atoms include methoxy, ethoxy, n-propoxy, n-butoxy group, t-butoxy group, n-pentyloxy, n-hexyloxy, and n-octyloxy.

Examples of the branched alkoxy group having 3 to 8 carbon atoms include isopropoxy, isobutoxy, cyclobutoxy, t-butoxy, isopentyloxy, neopentyloxy, and isooctyloxy.

The linear halogenated alkoxy group having 1 to 8 carbon atoms represents any of the above-described linear alkoxy groups having 1 to 8 carbon atoms in which at least one hydrogen atom is substituted with a halogen atom.

The branched halogenated alkoxy group having 3 to 8 carbon atoms represents any of the above-described branched alkoxy groups having 3 to 8 carbon atoms in which at least one hydrogen atom is substituted with a halogen atom.

Examples of the linear alkyl group having 1 to 8 carbon atoms, branched alkyl group having 3 to 8 carbon atoms, linear alkoxy group having 1 to 8 carbon atoms, branched alkoxy group having 3 to 8 carbon atoms and aryl group having 6 to 15 carbon atoms that may be represented by $X^2$ in Formula (I) include the same groups as those exemplified above for the group optionally substituting the hydrogen atoms in the groups represented by $X^1$ and $X^2$ in Formula (I).

Examples of the alkyl group having 1 to 6 carbon atoms that is represented by $Y^1$ to $Y^3$ in Formula (I) include methyl, ethyl, propyl, isopropyl, butyl, isobutyl, s-butyl, t-butyl, amyl, isoamyl, t-amyl, and hexyl.

Examples of the alkenyl group having 1 to 6 carbon atoms that is represented by $Y^1$ to $Y^3$ in Formula (I) include vinyl, ethylene, 2-propenyl, 3-butenyl, 2-butenyl, 4-pentenyl, 3-pentenyl, 2-hexenyl, 3-hexenyl, and 5-hexenyl.

The arylalkyl group having 7 to 13 carbon atoms that is represented by $Y^1$ to $Y^3$ in Formula (I) means an alkyl group having 7 to 13 carbon atoms in which a hydrogen atom is substituted with an aryl group. Examples thereof include benzyl, α-methylbenzyl, α,α-dimethylbenzyl, phenylethyl, and naphthylpropyl.

In the water-soluble composition of the present invention, compounds represented by Formula (I) wherein $X^1$ is phenyl, tolyl, xylyl, 2,4,6-trimethylphenyl or naphthyl are preferred since they are excellent in stability, absorption wavelength and solubility in water. Thereamong, an acylphosphinate represented by Formula (I) wherein $X^1$ is a 2,4,6-trimethylphenyl group is preferred since it imparts the water-soluble composition with high sensitivity.

In the water-soluble composition of the present invention, compounds represented by Formula (I) wherein $X^2$ is phenyl, tolyl, xylyl, 2,4,6-trimethylphenyl or naphthyl are preferred since they are excellent in stability, absorption wavelength and solubility in water. Thereamong, a compound represented by Formula (I) wherein $X^2$ is a phenyl group is preferred because of its high sensitivity.

In the water-soluble composition of the present invention, an acylphosphinate represented by Formula (I) wherein $X^2$ is a phenyl group and $A^{m+}$ is $N^+HY^1Y^2Y^3$ is preferred since it is highly soluble in water and imparts the water-soluble composition with high sensitivity. Preferred examples of $N^+HY^1Y^2Y^3$ include the following Compound Nos. A1 to A41. It is noted here, however, that the water-soluble composition of the present invention is not restricted at all by the following compounds.

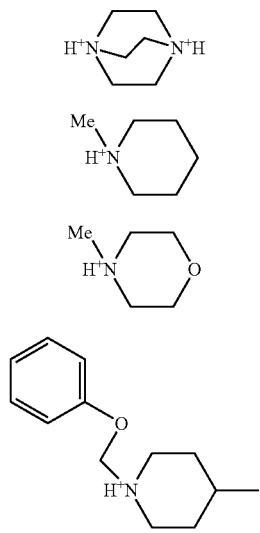

Compound No. A1

Compound No. A2

Compound No. A3

Compound No. A4

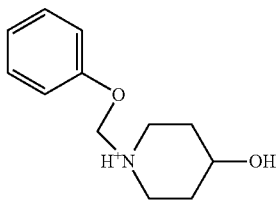

Compound No. A5

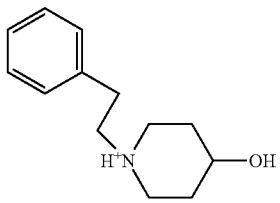

Compound No. A6

Compound No. A7

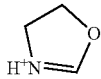

Compound No. A8

Compound No. A9

Compound No. A10

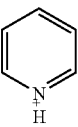

Compound No. A11

Compound No. A12

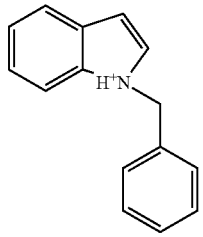

Compound No. A13

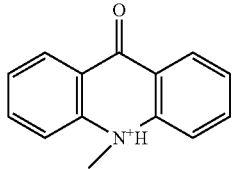

Compound No. A14

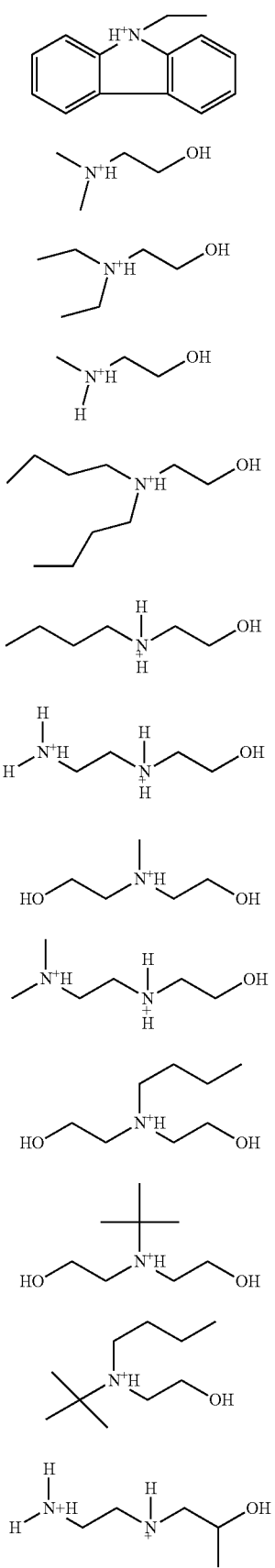

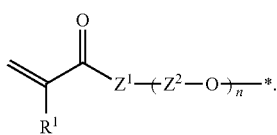

Compound No. 41

An acylphosphinate represented by Formula (I), wherein $X^2$ is a phenyl group, $A^{m+}$ is $N^+HY^1Y^2Y^3$ and one or more combinations of $Y^1$ and $Y^2$, $Y^1$ and $Y^3$, and $Y^2$ and $Y^3$ are bound with each other to form a ring, is particularly preferred since it is highly soluble in water and imparts the water-soluble composition with high sensitivity.

Preferred examples of $N^+HY^1Y^2Y^3$ in which one or more combinations of $Y^1$ and $Y^2$, $Y^1$ and $Y^3$, and $Y^2$ and $Y^3$ are bound with each other to form a ring include the above-described Compound Nos. A1 to A15.

The acylphosphinate (A), in which at least one hydrogen atom of $Y^1$ to $Y^3$ in the above-described $N^+HY^1Y^2Y^3$ is substituted with a hydroxy group, is preferred since it is highly compatible with water.

The content of the acylphosphinate (A) is 0.05 to 50 parts by mass, preferably 0.1 to 35 parts by mass, with respect to a total of 100 parts by mass of the acylphosphinate (A) and the compound (B). When the content of the acylphosphinate (A) is in this range, a water-soluble composition exhibiting good curability with a wide range of light sources, such as a high-pressure mercury lamp, an ultrahigh-pressure mercury lamp, an electrodeless lamp and an LED light source, can be obtained, and a cured product having a highly fine pattern can be obtained from this water-soluble composition, which are preferred.

<Compound (B)>

The compound (B) according to the water-soluble composition of the present invention is not particularly restricted as long as it contains a group represented by the following Formula (II):

$$\underset{R^1}{\overset{O}{\underset{\|}{\diagup\!\!\!\diagdown}}}Z^1-(Z^2-O)_n-*. \quad (II)$$

In Formula (II), $R^1$ represents a hydrogen atom or a methyl group; $Z^1$ represents an oxygen atom or $-NR^2-$; $R^2$ represents a hydrogen atom or a hydrocarbon group having 1 to 20 carbon atoms; $Z^2$ represents an alkylene group having 1 to 6 carbon atoms; n represents a number of 0 to 30; and * means a bond. When the compound (B) has plural groups represented by Formula (II), plural $R^1$'s, $Z^1$'s, $Z^2$'s and n's are each optionally the same or different.

The hydrocarbon group having 1 to 20 carbon atoms that is represented by $R^2$ in Formula (II) is not particularly restricted; however, it is preferably, for example, an alkyl group having 1 to 20 carbon atoms, an alkenyl group having 2 to 20 carbon atoms, a cycloalkyl group having 3 to 20 carbon atoms, a cycloalkylalkyl group having 4 to 20 carbon atoms, an aryl group having 6 to 20 carbon atoms, or an arylalkyl group having 7 to 20 carbon atoms. From the standpoint of imparting the water-soluble composition with good sensitivity, for example, an alkyl group having 1 to 10 carbon atoms, an alkenyl group having 2 to 10 carbon atoms, a cycloalkyl group having 3 to 10 carbon atoms, a cycloalkylalkyl group having 4 to 10 carbon atoms, an aryl group having 6 to 10 carbon atoms, or an arylalkyl group having 7 to 10 carbon atoms is more preferred.

Examples of the alkyl group having 1 to 20 carbon atoms include methyl, ethyl, propyl, isopropyl, butyl, isobutyl, s-butyl, t-butyl, amyl, isoamyl, t-amyl, hexyl, heptyl, octyl, isooctyl, 2-ethylhexyl, t-octyl, nonyl, isononyl, decyl, isodecyl, undecyl, dodecyl, tetradecyl, hexadecyl, octadecyl and icosyl, and examples of the alkyl group having 1 to 10 carbon atoms include methyl, ethyl, propyl, isopropyl, butyl, isobutyl, s-butyl, t-butyl, amyl, isoamyl, t-amyl, hexyl, heptyl, octyl, isooctyl, 2-ethylhexyl, t-octyl, nonyl, isononyl, decyl, and isodecyl.

Examples of the alkenyl group having 2 to 20 carbon atoms include vinyl, 2-propenyl, 3-butenyl, 2-butenyl, 4-pentenyl, 3-pentenyl, 2-hexenyl, 3-hexenyl, 5-hexenyl, 2-heptenyl, 3-heptenyl, 4-heptenyl, 3-octenyl, 3-nonenyl, 4-decenyl, 3-undecenyl, 4-dodecenyl, 3-cyclohexenyl, 2,5-cyclohexadienyl-1-methyl and 4,8,12-tetradecatrienylallyl, and examples of the alkenyl group having 2 to 10 carbon atoms include vinyl, 2-propenyl, 3-butenyl, 2-butenyl, 4-pentenyl, 3-pentenyl, 2-hexenyl, 3-hexenyl, 5-hexenyl, 2-heptenyl, 3-heptenyl, 4-heptenyl, 3-octenyl, 3-nonenyl, and 4-decenyl.

The "cycloalkyl group having 3 to 20 carbon atoms" means a saturated monocyclic or saturated polycyclic alkyl group having 3 to 20 carbon atoms. Examples thereof include cyclopropyl, cyclobutyl, cyclopentyl, cyclohexyl, cycloheptyl, cyclooctyl, cyclononyl, cyclodecyl, adamantyl, decahydronaphthyl, octahydropentalene, bicyclo[1.1.1]pentanyl and tetradecahydroanthracenyl, and examples of the cycloalkyl group having 3 to 10 carbon atoms include cyclopropyl, cyclobutyl, cyclopentyl, cyclohexyl, cycloheptyl, cyclooctyl, cyclononyl, cyclodecyl, adamantyl, decahydronaphthyl, octahydropentalene, and bicyclo[1.1.1]pentanyl.

The "cycloalkylalkyl group having 4 to 20 carbon atoms" means a group having 4 to 20 carbon atoms in which a hydrogen atom of an alkyl group is substituted with a cycloalkyl group. Examples thereof include cyclopropylmethyl, cyclobutylmethyl, cyclopentylmethyl, cyclohexylmethyl, cycloheptylmethyl, cyclooctylmethyl, cyclononylmethyl, cyclodecylmethyl, 2-cyclobutylethyl, 2-cyclopentylethyl, 2-cyclohexylethyl, 2-cycloheptylethyl, 2-cyclooctylethyl, 2-cyclononylethyl, 2-cyclodecylethyl, 3-cyclobutylpropyl, 3-cyclopentylpropyl, 3-cyclohexylpropyl, 3-cycloheptylpropyl, 3-cyclooctylpropyl, 3-cyclononylpropyl, 3-cyclodecylpropyl, 4-cyclobutylbutyl, 4-cyclopentylbutyl, 4-cyclohexylbutyl, 4-cycloheptylbutyl, 4-cyclooctylbutyl, 4-cyclononylbutyl, 4-cyclodecylbutyl, 3-3-adamantylpropyl and decahydronaphthylpropyl, and examples of the cycloalkylalkyl group having 4 to 10 carbon atoms include cyclopropylmethyl, cyclobutylmethyl, cyclopentylmethyl, cyclohexylmethyl, cycloheptylmethyl, cyclooctylmethyl, cyclononylmethyl, 2-cyclobutylethyl, 2-cyclopentylethyl, 2-cyclohexylethyl, 2-cycloheptylethyl, 2-cyclooctylethyl, 3-cyclobutylpropyl, 3-cyclopentylpropyl, 3-cyclohexylpropyl, 3-cycloheptylpropyl, 4-cyclobutylbutyl, 4-cyclopentylbutyl, and 4-cyclohexylbutyl.

Examples of the aryl group having 6 to 20 carbon atoms include phenyl, tolyl, xylyl, ethylphenyl, naphthyl, anthryl and phenanthrenyl, as well as phenyl, biphenylyl, naphthyl and anthryl which are substituted with at least one of the above-described alkyl groups, alkenyl groups, carboxyl group and halogen atoms, such as 4-chlorophenyl, 4-carboxylphenyl, 4-vinylphenyl, 4-methylphenyl and 2,4,6-trimethylphenyl, and examples of the aryl group having 6 to 10 carbon atoms include phenyl, tolyl, xylyl, ethylphenyl and naphthyl, as well as phenyl, biphenylyl, naphthyl and anthryl which are substituted with at least one of the above-described alkyl groups, alkenyl groups, carboxyl group and halogen atoms, such as 4-chlorophenyl, 4-carboxylphenyl, 4-vinylphenyl, 4-methylphenyl and 2,4,6-trimethylphenyl.

The "arylalkyl group having 7 to 20 carbon atoms" means a group having 7 to 20 carbon atoms in which a hydrogen atom of an alkyl group is substituted with an aryl group, and examples thereof include benzyl, α-methylbenzyl, α,α-dimethylbenzyl, phenylethyl, and naphthylpropyl. The "arylalkyl group having 7 to 10 carbon atoms" means a group having 7 to 10 carbon atoms in which a hydrogen atom of an alkyl group is substituted with an aryl group, and examples thereof include benzyl, α-methylbenzyl, α,α-dimethylbenzyl, and phenylethyl.

Examples of the alkylene group having 1 to 6 carbon atoms that is represented by $Z^2$ in Formula (II) include linear alkylene groups, such as a methylene group, an ethylene group, a propylene group, a butylene group, a pentylene group, and a hexylene group; and branched alkylene groups, such as an isopropylene group and an isobutylene group.

As the compound (B), for example, an alkylene oxide-modified (meth)acrylate compound or a (meth)acrylamide compound can be preferably used.

The "alkylene oxide-modified (meth)acrylate compound" means an alkylene oxide-modified acrylate compound or an alkylene oxide-modified methacrylate compound.

The "(meth)acrylamide compound" means an acrylamide compound or a methacrylamide compound.

The alkylene oxide-modified acrylate compound is a compound represented by Formula (II) wherein $R^1$ is a hydrogen atom, $Z^1$ is an oxygen atom and n is 1 to 30, and the alkylene oxide-modified methacrylate compound is a compound represented by Formula (II) wherein $R^1$ is a methyl group, $Z^1$ is an oxygen atom and n is 1 to 30.

Examples of the alkylene oxide-modified acrylate compound include diethylene oxide-modified neopentyl glycol diacrylate, dipropylene oxide-modified neopentyl glycol diacrylate, diethylene oxide-modified 1,6-hexanediol diacrylate and dipropylene oxide-modified 1,6-hexanediol diacrylate, and examples of the alkylene oxide-modified methacrylate compound include diethylene oxide-modified neopentyl glycol dimethacrylate, dipropylene oxide-modified neopentyl glycol dimethacrylate, diethylene oxide-modified 1,6-hexanediol dimethacrylate, and dipropylene oxide-modified 1,6-hexanediol dimethacrylate.

As the alkylene oxide-modified acrylate compound and the alkylene oxide-modified methacrylate compound, commercially available products can be preferably used as well, and examples thereof include NK ESTER A-600, A-GLY-20E, and NK ECONOMER A-PG5054E (all of which are manufactured by Shin Nakamura Chemical Co., Ltd.).

Among the above-exemplified alkylene oxide-modified acrylate compounds and alkylene oxide-modified methacrylate compounds, those in which $X^2$ of Formula (II) is an ethylene group or a propylene group are preferred because of their excellent solubility in water, and those in which $X^2$ of Formula (II) is an ethylene group are more preferred because of their particularly excellent solubility in water.

When the alkylene oxide-modified acrylate compound and the alkylene oxide-modified methacrylate compound contain a single group represented by Formula (II), n is particularly preferably 6 or larger since such compounds have excellent solubility in water. When the alkylene oxide-modified acrylate compound and the alkylene oxide-modified methacrylate compound contain plural groups represented by Formula (II), a sum of the values of n existing in a plural number is particularly preferably 10 or larger since such compounds have excellent solubility in water.

The above-described acrylamide compound is a compound represented by Formula (II) wherein $R^1$ is a hydrogen atom, $Z^1$ is —$NR^2$— and n is 0, and the above-described methacrylamide compound is a compound represented by Formula (II) wherein $R^1$ is a methyl group, $Z^1$ is —$NR^2$— and n is 0.

Examples of the acrylamide compound include hydroxyacrylamide, N-methylacrylamide, N-ethylacrylamide, N-isopropylacrylamide, N-butylacrylamide, diacetone acrylamide, N,N-dimethylacrylamide, N,N-diethylacrylamide, N,N-dipropylacrylamide, acryloylmorpholine, N-n-butoxymethylacrylamide, N-isobutoxymethylacrylamide and N-methoxymethylacrylamide, and examples of the methacrylamide compound include hydroxymethacrylamide, N-methylmethacrylamide, N-ethylmethacrylamide, N-isopropylmethacrylamide, N-butylmethacrylamide, diacetone methacrylamide, N,N-dimethylmethacrylamide, N,N-diethylmethacrylamide, N,N-dipropylmethacrylamide, methacryloylmorpholine, N-n-butoxymethylmethacrylamide, N-isobutoxymethylmethacrylamide, and N-methoxymethylmethacrylamide.

As the acrylamide compound and the methacrylamide compound, commercially available products can be preferably used as well, and examples thereof include FFM-2, FFM-3, FFM-4, and FFM-5 (which are manufactured by FUJIFILM Corporation).

The content of the compound (B) is 70 to 99.5 parts by mass, preferably 90 to 99.5 parts by mass, with respect to a total of 100 parts by mass of the acylphosphinate (A) and the compound (B). When the content of the compound (B) is in this range, a water-soluble composition exhibiting good curability with a wide range of light sources (LED) can be obtained, and a cured product having a highly fine pattern can be obtained from this water-soluble composition, which are preferred.

<Solvent>

The water-soluble composition of the present invention may also contain water as a solvent, and an organic solvent may be used in combination as well; however, the solvent is preferably water by itself from the standpoints of reducing the environmental load and inhibiting the deterioration of an organic material when the water-soluble composition is applied onto the organic material.

Examples of the organic solvent include solvents that are capable of dissolving or dispersing the above-described components (acylphosphinate (A) and compound (B)) and the like when used in combination with water, for example, ketones, such as methyl ethyl ketone, methyl amyl ketone, diethyl ketone, acetone, methyl isopropyl ketone, methyl isobutyl ketone, cyclohexanone, and 2-heptanone; ether-based solvents, such as ethyl ether, dioxane, tetrahydrofuran, 1,2-dimethoxyethane, 1,2-diethoxyethane, and dipropylene glycol dimethyl ether; ester-based solvents, such as methyl acetate, ethyl acetate, n-propyl acetate, isopropyl acetate, n-butyl acetate, cyclohexyl acetate, ethyl lactate, dimethyl succinate, and TEXANOL; cellosolve-based solvents, such as ethylene glycol monomethyl ether and ethylene glycol monoethyl ether; alcohol-based solvents, such as methanol, ethanol, iso- or n-propanol, iso- or n-butanol, and amyl alcohols; ether ester-based solvents, such as ethylene glycol monomethyl acetate, ethylene glycol monoethyl acetate, propylene glycol 1-monomethyl ether (PGM), propylene glycol 1-monomethyl ether 2-acetate (PGMEA), dipropylene glycol monomethyl ether acetate, 3-methoxybutyl acetate, and ethoxyethyl propionate; aromatic solvents, such as benzene, toluene, and xylene; aliphatic hydrocarbon-based solvents, such as hexane, heptane, octane, and cyclohexane; terpene-based hydrocarbon oils, such as turpentine oil, D-limonene, and pinene; paraffin-based solvents, such as mineral spirit, SWASOL #310 (manufactured by COSMO Matsuyama Oil Co., Ltd.) and SOLVESSO™ #100 (manufactured by Exon Chemical Co., Ltd.); halogenated aliphatic hydrocarbon-based solvents, such as carbon tetrachloride, chloroform, trichloroethylene, methylene chloride, and 1,2-dichloroethane; halogenated aromatic hydrocarbon-based solvents, such as chlorobenzene; carbitol-based solvents; aniline; triethylamine; pyridine; acetic acid; acetonitrile; carbon disulfide; N,N-dimethylformamide; N,N-dimethylacetamide; N-methylpyrrolidone; and dimethyl sulfoxide, among which alcohol-based solvents are preferred since they have good compatibility with water.

When any of the above-described solvents is used in the water-soluble composition of the present invention, the amount thereof is not particularly restricted; however, it is preferably 70 to 95% by mass with respect to the whole amount of the water-soluble composition. The content of the solvent is preferably in this range since this enables to obtain a curable composition having excellent ease of handling (viscosity and wettability of the curable composition) and excellent liquid stability (neither precipitation nor sedimentation of a component contained in the composition occurs) and to appropriately control the thickness of the resulting cured product.

<Other>

In the water-soluble composition of the present invention, as required, for example, a water-soluble polymer having both a photosensitive group and a hydroxy group, a polyvinyl alcohol-modified water-soluble polymer, a crosslinking agent, a water-soluble polymer having neither a photosensitive group nor a partial structure represented by the below-described Formula (VI), an organic acid, a coupling agent, a sensitizer, a surfactant, a basic compound, a coloring agent, a radical initiator (excluding the acylphosphinate (A)), a water-soluble preservative, and/or a conductive substance may be incorporated as well.

Preferred examples of the water-soluble polymer having both a photosensitive group and a hydroxy group include compounds having any of Formulae (IIIα) to (IIIε) below as a structural unit since such compounds yield cured products having high heat resistance, water resistance and moist-heat resistance and, thereamong, ones having Formulae (IIIδ) and (IIIε) as structural units are more preferred since such compounds yield water-soluble compositions having excellent curability even with the use of an LED light source (365 nm) as well as cured products having excellent heat resistance, water resistance and moist-heat resistance.

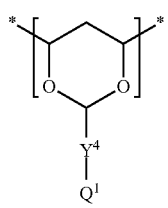
(IIIα)

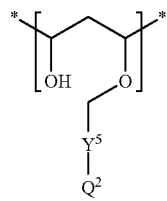
(IIIβ)

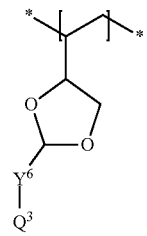
(IIIγ)

wherein, $Y^4$, $Y^5$ and $Y^6$ each independently represent a direct bond or a divalent linking group; $Q^1$, $Q^2$ and $Q^3$ each independently represent a photosensitive group; and * represents a bond.

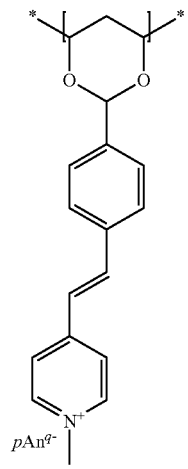
(IIIδ)

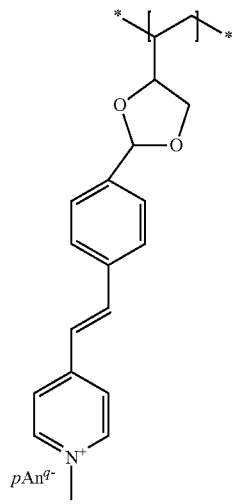
(IIIε)

wherein, An$^{q-}$ represents a q-valent anion; q represents 1 or 2; p represents a coefficient that maintains a neutral charge; and * means a bond.

The divalent linking group represented by Y$^4$, Y$^5$ and Y$^6$ in Formulae (IIIα), (IIIβ) and (IIIγ) is not particularly restricted; however, preferred examples thereof include alkylene groups having 1 to 10 carbon atoms, such as a methylene group, an ethylene group, a trimethylene group, a propylene group, and a butylene group; arylene groups having 6 to 30 carbon atoms, such as a phenylene group and a naphthalene group; heterocyclic linking groups; —CH=CH—; —O—; —S—; —C(=O)—; —CO—; —NR—; —CONR—; —OC—; —SO—; —SO$_2$—; and linking groups constituted by a combination of two or more of these groups. It is noted here that Rs each independently represent a hydrogen atom, an alkyl group, an aryl group, or a heterocyclic group.

Examples of the photosensitive group represented by Q$^1$, Q$^2$ and Q$^3$ in Formulae (IIIα), (IIIβ) and (IIIγ) include a cinnamyl group, a cinnamoyl group, a cinnamylidene group, a cinnamylideneacetyl group, a chalcone group, a coumarin group, an isocoumarin group, a 2,5-dimethoxystilbene group, a maleimide group, an α-phenylmaleimide group, a 2-pyrone group, an azide group, a thymine group, a quinone group, a uracil group, a pyrimidine group, a stilbazolium group, a styrylpyridinium group, a styrylquinolium group, an epoxy group, an oxetane group, a vinyl ether group, an allyl ether group, an acryl group, a methacryl group, an acrylamide group, a methacrylamide group, a vinyl group, an allyl group, and a styryl group, among which a stilbazolium group, a cinnamoyl group, an acryl group, a methacryl group, an acrylamide group, or a methacrylamide group can be preferably used since a water-soluble composition having high photosensitivity and high liquid stability (not involving an increase in viscosity, gelation, precipitation and the like) is thereby obtained.

Among the above-exemplified photosensitive groups, a stilbazolium group is highly soluble in water and has an absorption band at about 365 nm; therefore, the use thereof enables to obtain a water-soluble composition that exhibits photosensitivity even for a light source having a long wavelength, such as an LED light source (365 nm). This water-soluble composition can be particularly preferably used since it yields a cured product having a highly fine pattern in addition to heat resistance, water resistance and moist-heat resistance.

Specific examples of a preferred water-soluble polymer having a photosensitive group and a hydroxy group include water-soluble photosensitive polymers represented by the following Formulae (IV) and (V).

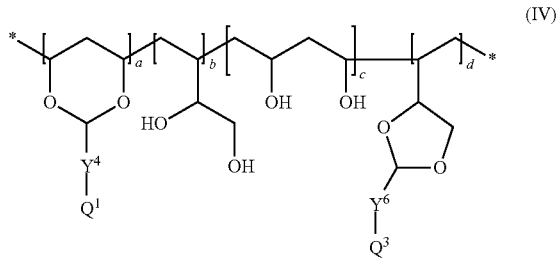
(IV)

wherein, Y$^4$ and Q$^1$ are the same as in the above-described Formula (IIIα); Y$^6$ and Q$^3$ are the same as in the above-described Formula (IIIγ); a, b, c and d each represent a number of 0 to 5,000, with a and d not being 0 at the same time and a relationship of 100<a+b+c+d<5,000 being satisfied; and * represents a bond.

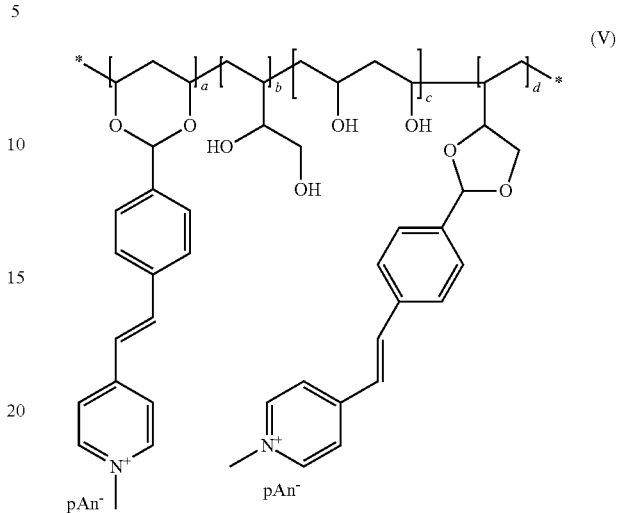

wherein, a, b, c and d are the same as in Formula (IV), with a and d not being 0 at the same time and a relationship of 100<a+b+c+d<5,000 being satisfied; and * represents a bond.

In Formulae (IV) and (V), from the standpoint of allowing a cured product obtained from the water-soluble composition of the present invention to have good heat resistance and adhesiveness, the values of a, b, c and d (molar ratio) are preferably a:b:c:d=0.1 to 4:5 to 30:5 to 70:0.1 to 4, and the weight-average molecular weight of the polymer is 15,000 to 5,000,000, preferably 100,000 to 1,000,000.

A polymer represented by Formula (V) can be obtained by performing an acetalization reaction between a butenediol-polyvinyl alcohol copolymer and a photosensitive group-containing aldehyde under a condition of pH 1 to 4. A polymer represented by Formula (V) can also be produced using commercially available products and, for example, it can be obtained by performing an acetalization reaction between a G-POLYMER (butenediol-vinyl alcohol copolymer) OKS-1081, OKS-1083 or OKS-1109 and a photosensitive group-containing aldehyde under a condition of pH 1 to 4.

The term "polyvinyl alcohol-modified water-soluble polymer" used herein refers to a water-soluble polymer whose structure does not contain the above-described photosensitive group but has a structural unit represented by the following Formula (VI), and this water-soluble polymer can improve the heat resistance of the resulting cured product when added in combination with the below-described cross-linking agent.

(VI)

wherein, * represents a bond.

In the polyvinyl alcohol-modified water-soluble polymer, the main chain is the same as in a conventionally known polyvinyl alcohol, and examples thereof include polyvinyl alcohols, partially saponified polyvinyl alcohols and completely saponified polyvinyl alcohols, which are obtained by polymerization of vinyl alcohols and generally referred to as "povals"; and saponification products of copolymers composed of vinyl acetate and a monomer copolymerizable therewith. The polyvinyl alcohol constituting the polyvinyl alcohol-modified water-soluble polymer may be a homopolymer or a copolymer that contains a vinyl alcohol as an essential monomer.

A method of producing the polyvinyl alcohol-modified water-soluble polymer is not particularly restricted, and examples thereof include a method of allowing a polyvinyl alcohol to react with diketene, a method of allowing a polyvinyl alcohol to react with an acetoacetic ester to perform transesterification, and a method of saponifying a copolymer of vinyl acetate and vinyl acetoacetate. Thereamong, a method of allowing a polyvinyl alcohol to react with diketene is preferably employed to produce the polyvinyl alcohol-modified water-soluble polymer since this method yields a good-quality acetoacetate group-containing polyvinyl alcohol in a simple production process.

Examples of the monomer copolymerizable with vinyl acetate include unsaturated carboxylic acids, such as maleic acid, maleic anhydride, fumaric acid, crotonic acid, itaconic acid, acrylic acid and methacrylic acid, and esters of these unsaturated carboxylic acids; α-olefins, such as ethylene and propylene; allyl sulfonic acid; methallyl sulfonic acid; sodium allylsulfonate; sodium methallylsulfonate; sodium sulfonate; sodium sulfonate monoalkyl maleate; sodium disulfonate alkyl maleate; N-methylolacrylamide; acrylamide alkylsulfonate alkali salts; N-vinylpyrrolidone; and N-vinylpyrrolidone derivatives, and these monomers account for preferably 10% by mole or less, particularly preferably 5% by mole, of all structural units. An excessively large amount of these monomers may reduce the solubility in water.

By adding a polyvinyl alcohol-modified water-soluble polymer which has a polystyrene-equivalent weight-average molecular weight (Mw) of 10,000 to 200,000 as determined by gel permeation chromatography (GPC) and a saponification degree (hydrolysis rate) of 85 to 100 along with the below-described crosslinking agent to the water-soluble composition of the present invention, the water resistance and the film durability of the resulting cured product are improved, which is preferred, and a polyvinyl alcohol-modified water-soluble polymer having a saponification degree of 95 to 100 is more preferred since it further improves the water resistance.

The use of a compound having a structural unit represented by the following Formula (VII) as the polyvinyl alcohol-modified water-soluble polymer is more preferred since it allows a cured product obtained from the water-soluble composition of the present invention to have particularly excellent heat resistance, water resistance and moist-heat resistance:

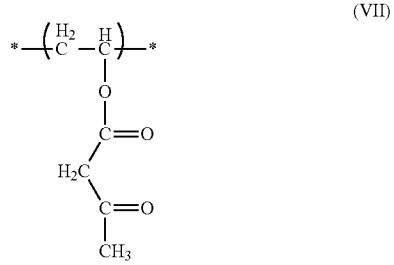

(VII)

Usually, the content of the structural unit represented by Formula (VII) is preferably 0.1 to 20% by mole, more preferably 0.2 to 15% by mole, particularly preferably 0.3 to 10% by mole, from the standpoints of the water resistance, the crosslinking rate, the solubility in water, and the aqueous solution stability of the cured product.

As the polyvinyl alcohol-modified water-soluble polymer, a commercially available product may be used as well, and examples thereof include GOHSENX™ Z-100, Z-200, Z-220, Z-300 and Z-410 (which are manufactured by The Nippon Synthetic Chemical Industry Co., Ltd.).

As the crosslinking agent, any crosslinking agent can be used with no restriction as long as it is capable of crosslinking the polyvinyl alcohol-modified water-soluble polymer. As the crosslinking agent, for example, a conventionally known organic crosslinking agent, a chelating agent-containing metal chelate complex, a zirconium compound, or a titanium compound can be preferably used.

The organic crosslinking agent can be arbitrarily selected from those compounds and resins that are commonly used as crosslinking agents, and examples thereof include bisazide compounds, amino resins having a hydroxyl group or an alkoxyl group, polyethylene imines, melamine resins, urea resins, guanamine resins, glycoluril-formaldehyde resins, succinylamide-formaldehyde resins, and ethylene urea-formaldehyde resins. As these crosslinking agents, melamine, urea, guanamine, glycoluril, succinylamide and ethylene urea that are each methylolated through reaction with formalin in boiling water, or the resultants thereof further alkoxylated through reaction with a lower alcohol, can be used.

Examples of the chelating agent include hydroxycarboxylic acids and salts thereof, glyoxylic acid and salts thereof, amino alcohols, aminocarboxylic acids, alanine, arginine, leucine, isoleucine, dihydroxypropyl glycine, ethylenediamine tetraacetic acid, diethylenetriamine pentaacetic acid, nitrilotriacetic acid, β-diketone, dimethyl glyoxime, citric acid, tartaric acid, maleic acid, polyhydrazide and phosphoric acid esters, and these chelating agents may be used individually, or in combination of two or more thereof.

The use of a metal chelate complex containing a chelating ligand that can be coordinated at two or more sites by covalent bonds, hydrogen bonds or the like with respect to a single metal atom is preferred since the crosslinking reaction rate is thereby adjusted appropriately. Specific examples of a chelating ligand include hydroxycarboxylic acids and salts thereof, aminoalcohols, and β-diketones.

Examples of the zirconium compound include zirconium halides, such as zirconium oxychloride, zirconium hydroxychloride, zirconium tetrachloride, and zirconium bromide; zirconium salts of mineral acids, such as zirconium sulfate, basic zirconium sulfate, zirconium oxynitrate, zirconium oxyacetate, and zirconium oxycarbonate; zirconium salts of organic acids, such as zirconium formate, zirconium acetate, zirconium propionate, zirconium caprylate, zirconium stearate, zirconium lactate, zirconium nitrate, zirconium carbonate, zirconium octylate, zirconium citrate, and zirconium phosphate; zirconium complex salts, such as ammonium zirconium carbonate, sodium zirconium sulfate, ammonium zirconium acetate, ammonium zirconium carbonate, potassium zirconium carbonate, sodium zirconium oxalate, sodium zirconium citrate, ammonium zirconium citrate, and zirconium lactate ammonium; and zirconium chelate complexes containing one or more chelating agents as ligands. Thereamong, water-soluble zirconium is preferred, and zirconium oxyhalides, zirconium oxyacetate, zirconium sulfate and zirconium oxynitrate are more preferred.

Examples of the zirconium chelate complexes include zirconium tetraacetylacetonate, zirconium monoacetylacetonate, zirconium oxyhalides, zirconium oxynitrate, zirconium lactate ammonium, zirconium sulfate, zirconium oxyacetate, zirconium bis-acetylacetonate, zirconium monoethylacetoacetate, and zirconium acetate.

Among these zirconium compounds, for example, zirconium tetraacetylacetonate, zirconium monoacetylacetonate, zirconium oxyhalides, zirconium oxynitrate, zirconium lactate ammonium, zirconium sulfate, and zirconium oxyacetate are preferred because of their high stability, solubility in water and reactivity. These zirconium compounds may be used individually, or in combination of two or more thereof as a mixture.

As the zirconium compound, a commercially available product can be used as well, and examples thereof include zirconium oxychloride, ZIRCOSOL ZC-2, ZIRCOSOL ZN, ZIRCOSOL HA, ZIRCOSOL AC-7, ZIRCOSOL ZK-10, ZIRCOSOL ZN, ZIRCOSOL ZA-10, ZIRCOSOL ZA-20, zirconyl octylate, and zirconyl carbonate (which are manufactured by Daiichi Kigenso Kagaku Kogyo Co., Ltd.); and ORGATIX ZA-45, ORGATIX ZA-65, ORGATIX ZB-126, ORGATIX ZC-126, ORGATIX ZC-150, ORGATIX ZC-200, ORGATIX ZC-300, ORGATIX ZC-320, ORGATIX ZC-540, ORGATIX ZC-580, ORGATIX ZC-700, and ZC-300 (which are manufactured by Matsumoto Fine Chemical Co., Ltd.).

Examples of the titanium compound include titanium alkoxides, such as tetramethyl titanate, tetraethyl titanate, tetra-n-propyl titanate, tetraisopropyl titanate, tetra-n-butyl titanate, tetraisobutyl titanate, tetra-t-butyl titanate, tetraoctyl titanate, tetra(2-ethylhexyl) titanate, and tetramethyl titanate; oligomers and polymers that are obtained by hydrolysis reaction of a titanium alkoxide, such as a titanium butyl dimer and a titanium butyl tetramer, and derivatives thereof; titanium chelate complexes, such as titanium acetylacetonate, titanium octylene glycolate, titanium tetraacetylacetonate, titanium ethylacetoacetate, titanium triethanol aluminate, and titanium oxalate; titanium acylates, such as polyhydroxytitanium stearate; titanium tetrachloride; titanium lactate; titanium triethanol aminate; and diisopropoxytitanium bis(triethanolaminate), and these titanium compounds may be used individually, or in combination of two or more thereof as a mixture.

As the titanium compound, a commercially available product can be used as well, and examples thereof include ORGATIX TA-8, ORGATIX TA-10, ORGATIX TA-12, ORGATIX TC-100, ORGATIX TC-120, ORGATIX TC-300, ORGATIX TC-310, ORGATIX TC-315, ORGATIX TC-335, ORGATIX TC-401, ORGATIX TC-800, and ORGATIX WS-700 (which are manufactured by Matsumoto Fine Chemical Co., Ltd.); and TITA BOND T-100, TITA BOND T-120, TITA BOND T-120A, TITA BOND T-150, TITA BOND T-160, TITA BOND T-180E, and TITA BOND T-185E (which are manufactured by Nippon Soda Co., Ltd.).

Among the above-described crosslinking agents, a zirconium compound or a titanium compound is particularly preferred from the standpoint of allowing a cured product obtained from the water-soluble composition of the present invention to have good moist-heat resistance.

When a crosslinking agent and a polyvinyl alcohol-modified water-soluble polymer are added, the crosslinking agent is added in an amount of preferably 0.01 to 5 parts by mass with respect to 100 parts by mass of the polyvinyl alcohol-modified water-soluble polymer since this makes the water-soluble composition stable without any change such as precipitation or an increase in viscosity.

The water-soluble composition of the present invention contains a metal component derived from the crosslinking agent, and the metal content in the components excluding the solvent of the water-soluble composition is preferably 0.01 to 3% by mass, more preferably 0.01 to 1% by mass.

Examples of the water-soluble polymer having neither the above-described photosensitive group nor the above-described partial structure represented by Formula (VI) include oxidized starch; etherified, esterified or grafted modified starch; cellulose derivatives, such as gelatin, casein, and carboxymethylcellulose; polyvinylpyrrolidones; water-soluble resins, such as water-soluble polyester resins, water-soluble polyacrylic acid ester resins (e.g., 2-hydroxypropyl acrylate polymers and 4-hydroxybutyl acrylate polymers), water-soluble polycarbonate resins, water-soluble polyvinyl acetate resins, water-soluble styrene acrylate resins, water-soluble vinyltoluene acrylate resins, water-soluble polyurethane resins, water-soluble polyamide resins (e.g., polyvinylamide, polyacrylamide, and modified acrylamide), water-soluble urea resins, water-soluble polycaprolactone resins, water-soluble polystyrene resins, water-soluble polyvinyl chloride resins, water-soluble polyacrylate resins, and water-soluble polyacrylonitrile resins; styrene-butadiene copolymers; acrylate copolymers; and ethylene-vinyl acetate copolymers.

As the above-described organic acid, any carboxyl group-containing weakly acidic compound can be used with no restriction, and examples thereof include acetic acid, citric acid, malic acid, glycolic acid, lactic acid, carbonic acid, formic acid, oxalic acid, propionic acid, octylic acid, caprylic acid, glucuronic acid, stearic acid, benzoic acid, and mandelic acid. Thereamong, the organic acid is preferably lactic acid, acetic acid, citric acid, glycolic acid, or malic acid.

Examples of the above-described coupling agent that can be used include alkyl functional alkoxysilanes, such as dimethyldimethoxysilane, dimethyldiethoxysilane, methylethyldimethoxysilane, methylethyldiethoxysilane, methyltrimethoxysilane, methyltriethoxysilane, ethyltrimethoxysilane, and ethyltrimethoxysilane; alkenyl functional alkoxysilanes, such as vinyltrichlorosilane, vinyltrimethoxysilane, vinyltriethoxysilane, and allyltrimethoxysilane; epoxy functional alkoxysilanes, such as 3-methacryloxypropyltriethoxysilane, 3-methacryloxypropyltrimethoxysilane, 3-methacryloxypropylmethyldiethoxysilane, 3-methacryloxypropylmethyldimethoxysilane, 2-methacryloxypropyltrimethoxysilane, γ-glycidoxypropyltrimethoxysilane, γ-glycidoxypropylmethyldiethoxysilane, and β-(3,4-epoxycyclohexypethyltrimethoxysilane; amino functional alkoxysilanes, such as N-β(aminoethyl)-γ-aminopropyltrimethoxysilane, γ-aminopropyltriethoxysilane, and N-phenyl-γ-aminopropyltrimethoxysilane; and mercapto functional alkoxysilanes, such as γ-mercaptopropyltrimethoxysilane.

The above-described sensitizer is a compound that is capable of expanding the wavelength range of applicable light when curing is performed by irradiation with light and, as the sensitizer, for example, thioxanthones described in JP2005-307199A, thioxanthones described in JP2012-7071A, and benzophenones, thioxanthones, thiochromanones and biimidazoles described in WO2014/050551 are preferred.

Examples of sensitizers other than the above-described ones include α-aminoacetophenones; α-hydroxyacetophenones; benzyl ketals; benzophenones, such as benzophenone, 3-hydroxybenzophenone, 4-hydroxybenzophenone, 4,4-dihydroxybenzophenone, 2-methylbenzophenone, 3-methylbenzophenone, 4-methylbenzophenone, 2,5-dimethylbenzophenone, 3,4-dimethylbenzophenone, 4-methoxybenzophenone, 4,4-dimethoxybenzophenone, 3,3-dimethyl-4-methoxybenzophenone, and 4-phenylbenzophenone; acetophenones, such as acetophenone, 4-methoxyacetophenone, 2,4-dimethoxyacetophenone, 2,5-dimethoxyacetophenone, 2,6-dimethoxyacetophenone, 4,4-dimethoxyacetophenone, 4-ethoxyacetophenone, diethoxyacetophenone, 2,2-diethoxyacetophenone, 2-ethoxy-2-phenylacetophenone, and 4-phenylacetophenone; anthraquinones, such as anthraquinone, hydroxyanthraquinone, 1-nitroanthraquinone, aminoanthraquinone, 2-chloroanthraquinone, 2-methylanthraquinone, 2-ethylanthraquinone, anthraquinone sulfonic acid, 1,2-benzanthraquinone, and 1,4-hydroxyanthraquinone (quinizarin); anthracenes, such as anthracene, 1,2-benzanthracene, 9-cyanoanthracene, 9,10-dicyanoanthracene, 2-ethyl-9,10-dimethoxyanthracene, and 9,10-bis(phenylethyl)anthracene; quinones, such as 2,3-dichloro-6-dicyano-p-benzoquinone, 2,3-dimethoxy-5-methyl-1,4-benzoquinone, methoxybenzoquinone, 2,5-dichloro-p-benzoquinone, 2,6-dimethyl-1,4-benzoquinone, 9,10-phenanthrenequinone, camphor quinone, 2,3-dichloro-1,4-naphthoquinone, and xanthone; thioxanes, such as thioxanthone, 2-methylthioxanthone, 2,4-dimethylthioxanthone, isopropylthioxanthone, 2,4-diethylthioxanthone, and 2,4-isopropylthioxanthone; cycloheptanes, such as dibenzosuberone, dibenzosuberenone, dibenzosuberenol, and dibenzosuberane; aromatic compounds, such as 2-methoxynaphthalene, benzoin isopropyl ether, 4-benzoyldiphenyl, o-benzoyl benzoate, methyl o-benzoylbenzoate, 4-benzoyl-4-methyl-diphenyl sulfide, benzyl, and benzoin methyl ether; and coumarin-based, thiazine-based, azine-based, acridine-based, and xanthene-based compounds that are dye-based sensitizing substances. Among these sensitizers, benzophenones, thioxanthones, thiochromanones, biimidazoles, α-aminoacetophenones, α-hydroxyacetophenones, and benzyl ketals are preferred from the standpoint of their high stability particularly in water (unlikeliness of being hydrolyzed).

Examples of the above-described surfactant that can be used include fluorine surfactants, such as perfluoroalkyl phosphates and perfluoroalkyl carboxylates; anionic surfactants, such as higher fatty acid alkali salts, alkyl sulfonates, and alkyl sulfates; cationic surfactants, such as higher amine halogen acid salts and quaternary ammonium salts; nonionic surfactants, such as polyethylene glycol alkyl ethers, polyethylene glycol fatty acid esters, sorbitan fatty acid esters, and fatty acid monoglycerides; amphoteric surfactants; and silicone-based surfactants, and these surfactants may be used in combination.

Examples of the above-described basic compound include ammonia, sodium hydroxide, potassium hydroxide, triethylamine, triethanolamine, diethanolamine, monoethanolamine, triisopropanolamine, diisopropanolamine, monoisopropanolamine, N,N-dimethylethanolamine, ethylene imine, pyrrolidine, piperidine, polyethyleneimine and tetramethylammonium hydroxide, and these basic compounds may be used individually, or in combination of two or more thereof. These basic compounds may be added for the purposes of pH adjustment and the like.

As the above-described coloring agent, a pigment or a dye can be used. The pigment or the dye can each be an inorganic or organic color material, and such a color material may be used individually, or in combination of two or more thereof. The term "pigment" used herein refers to a coloring agent insoluble in the below-described solvents and also encompasses inorganic and organic color materials that are insoluble in solvents, as well as laked inorganic and organic dyes.

Examples of the pigment include carbon blacks, such as those obtained by a furnace process, a channel process or a thermal process, acetylene black, Ketjen black, and lamp black; the above-described carbon blacks that have been adjusted or coated with an epoxy resin; the above-described carbon blacks that have been dispersed in a solvent together with a resin in advance and thereby coated with 20 to 200 mg/g of the resin; the above-described carbon blacks that have been subjected to a surface treatment with an acid or an alkali; carbon blacks having an average particle size of 8 nm or larger and a DBP oil absorption of 90 ml/100 g or less; carbon blacks having a total oxygen content, which is calculated from the CO and $CO_2$ content in a volatile component at 950° C., of not less than 9 mg per 100 $m^2$ of the surface area; graphitized carbon blacks; graphites; activated carbons; carbon fibers; carbon nanotubes; carbon microcoils; carbon nanohorns; carbon aerogels; fullerene; black pigments represented by aniline black, PIGMENT BLACK 7 and titanium black; and organic and inorganic pigments, such as chromium oxide green, Milori blue, cobalt green, cobalt blue, manganese-based pigments, ferrocyanides, phosphate ultramarine blue, Prussian blue, ultramarine, cerulean blue, viridian, emerald green, lead sulfate, lead yellow, zinc yellow, Indian red (red iron (III) oxide), cadmium red, synthetic iron black, amber, and lake pigments. Thereamong, it is preferred to use a black pigment because of its high light-shielding property, and it is more preferred to use a carbon black as a black pigment.

As the pigment, a commercially available pigment can be used as well, and examples thereof include MICROPIGMO® WMYW-5, MICROPIGMO® WMRD-5, MICROPIGMO® WMBN-5, MICROPIGMO® WMGN-5, MICROPIGMO® WMBK-5, MICROPIGMO® WMBE-5, MICROPIGMO® WMVT-5, MICROPIGMO® WMWE-1, and BONJET® BLACK CW-1 (all of which are manufactured by Orient Chemical Industries Co., Ltd.); PIGMENT RED 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 254, 228, 240, and 254; PIGMENT ORANGE 13, 31, 34, 36, 38, 43, 46, 48, 49, 51, 52, 55, 59, 60, 61, 62, 64, 65, and 71; PIGMENT YELLOW 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; PIGMENT GREEN 7, 10, 36, and 58; PIGMENT BLUE 15, 15:1, 15:2, 15:3, 15:4, 15:5, 15:6, 22, 24, 56, 60, 61, 62, and 64; and PIGMENT VIOLET 1, 19, 23, 27, 29, 30, 32, 37, 40, and 50.

Examples of the dye include nitroso compounds, nitro compounds, azo compounds, diazo compounds, xanthene compounds, quinoline compounds, anthraquinone compounds, coumarin compounds, cyanine compounds, phthalocyanine compounds, isoindolinone compounds, isoindoline compounds, quinacridone compounds, anthanthrone compounds, perinone compounds, perylene compounds, diketopyrrolopyrrole compounds, thioindigo compounds, dioxazine compounds, triphenylmethane compounds, quinophthalone compounds, naphthalene tetracarboxylic acids, and metal complex compounds of azo dyes and cyanine dyes.

As the dye, a water-soluble dye or an oil-soluble dye can be used as appropriate.

As the dye, a commercially available dye can be used as well, and examples thereof include WATER YELLOW 1, WATER YELLOW 2, WATER YELLOW 6C, WATER YELLOW 6CL, WATER ORANGE 18, WATER ORANGE 25, WATER RED 1, WATER RED 2S, WATER RED 3, WATER RED 9, WATER RED 27, WATER PINK 2S, WATER BROWN 16, WATER GREEN 8, WATER BLUE 3, WATER BLUE 9, WATER BLUE 105S, WATER BLUE 106, WATER BLUE 117-L, WATER VIOLET 7, WATER BLACK 31, WATER BLACK 191-L, WATER BLACK 256-L, WATER BLACK R-455, WATER BLACK R-510, BONJET® YELLOW 161-L, BONJET® MAGENTA XXX, BONJET® CYAN XXX, BONJET® BLACK 891-L, VALIFAST® YELLOW 1101, VALIFAST® YELLOW 3150, VALIFAST® RED 1308, VALIFAST®® RED 2320, VALIFAST® PINK 1364, VALIFAST PINK 2310N, VALIFAST® VIOLET 1701, VALIFAST® BLACK 1815, VALIFAST® BLACK 1807, VALIFAST® BLACK 3804, VALIFAST® BLACK 3810, VALIFAST® BLACK 3820, VALIFAST® BLACK 3830, VALIFAST® BLACK 3840, VALIFAST® BLACK 3866, VALIFAST® BLACK 3870, VALIFAST® ORANGE 2210, VALIFAST® BROWN 3402, VALIFAST® BLUE 1613, and VALIFAST® BLUE 1605 (all of which are manufactured by Orient Chemical Industries Co., Ltd.); ACID GREEN 1, ACID GREEN 3, ACID GREEN 5, ACID GREEN 9, ACID GREEN 27, ACID GREEN 50, ACID GREEN A, ALIZARIN CYANIN GREEN F, BASIC GREEN 1, BASIC GREEN 5, BROMOCRESOL GREEN, BROMOCRESOL GREEN Sodium Salt, ERIO GREEN B, FAST GREEN FCF, FITER BLUE GREEN Sodium Salt, INDOCYANINE GREEN, JANUS GREEN B, LEUCO MALACHITE GREEN, MALACHITE GREEN, OXALATE, METHYL GREEN, PALATINE CHROME GREEN, QUINIZARIN GREEN SS, ACID RED 1, ACID RED 9, ACID RED 13, ACID RED 18, ACID RED 26, ACID RED 27, ACID RED 52, ACID RED 87, ACID RED 88, ACID RED 91, ACID RED 92, ACID RED 94, ACID RED 112, ACID RED 114, ACID RED 151, ACID RED 289, ALIZARIN, ALLURA RED AC, ASTRAZON RED 6B, AZO RUBINE, BASIC RED 5, BENZOPURPURINE 4B, BORDEZUX RED, CHLORANTINE FAST RED 5B, CHROMOTROPE 2B, CHROMOTROPE 2R, CONGO RED, CRESOL RED, CREZOL RED Sodium Salt, CROCEIN SCARLET 3B, DIRECT FAST RED 3B, DIRECT RED 80, DIRECT SCARLET B, ERIOCHROME RED B, 4-ethoxychrysoidine hydrochloride, ETHYL RED, FAST RED B Salt, FAST RED ITR Base, LAKE RED CBA, LITHOL RUBIN BCA, METHOXY RED, METHYL RED, METHYL RED Sodium Salt, ORALITH BRILLIANT PINK R, PARA RED, PHENOL RED Sodium Salt, PIGMENT RED, PIGMENT RED 254, RHODAMINE 6G SUDAN II, SUDAN III, SUDAN R, 2,3,5-triphenyltetrazolium chloride, ACID BLACK 1, ACID BLUE 1, ACID BLUE 9, ACID BLUE 92, ACID BLUE 3 Sodium Salt, ACID RED 91, AZO BLUE, BASIC BLUE 1, BASIC BLUE 7, BASIC BLUE 12, BASIC BLUE 17, BASIC BLUE 24, BASIC BLUE 26, BRILLIANT BLUE G, BRILLIANT BLUE R, BROMOCRESOL BLUE, BROMOPHENOL BLUE, BROMOTHYMOL BLUE, CHROME PURE BLUE BX, COOMASSIE BRILLIANT BLUE G-250, COOMASSIE BRILLIANT BLUE R-250, DIRECT BLUE 1, DIRECT BLUE 2, DIRECT BLUE 14, DIRECT SKY BLUE, DISPERSE BLUE 14, ERIOCHROME BLUE BLACK B, ERIOCHROME CYANINE R, EVANS BLUE, FILTER BLUE GREEN Sodium Salt, INDIGO CARMINE, INDIGO, METHYLENE BLUE HYDRATE, MORDANT BLACK 17, MORDANT BLUE 13, MORDANT BLUE 29, OMEGA CHROME BLACK BLUE G, PIGMENT BLUE 15, QUINIZARIN BLUE, SUDAN BLUE, THYMOL BLUE, XYLENE CYANOL FF, ACID ORANGE 5, ACID ORANGE 7, 1-amino-2-methylanthraquione, ASTRAZON ORANGE R, BASIC ORANGE 14, CROCEIN ORANGE G, ETHYL ORANGE, METHYL ORANGE, MORDANT ORANGE 1, α-NAPHTHOL ORANGE, OIL ORANGE, ORANGE G, PERMANENT ORANGE, PYRAZOLONE ORANGE, SUDAN I, and SUDAN II (all of which are manufactured by Tokyo Chemical Industry Co., Ltd.).

As the radical initiator (excluding the acylphosphinate (A)), a conventionally known compound can be used, and examples thereof include those described in JPH06-228218A, JP2009-102455A, JP2012-007071A, JPH06-239910A, JP2003-192712A and JP2016-185929A and WO2014/050551, as well as hydrogen abstraction-type photopolymerization initiators, such as benzophenone, thioxanthone, 1-chloro-4-propoxythioxanthone, isopropylthioxanthone, diethylthioxanthone, and ethylanthraquinone; and photolytic photopolymerization initiators, such as phenyl biphenyl ketone, 1-hydroxy-1-benzoylcyclohexane (α-hydroxyalkylphenone), benzoin, benzyl dimethyl ketal, 1-benzyl-1-dimethylamino-1-(4'-morpholinobenzoyl)propane, 2-morpholyl-2-(4'-methylmercapto)benzoylpropane, 4-benzoyl-4'-methyldiphenyl sulfide, benzoin butyl ether, 2-hydroxy-2-benzoylpropane, 2-hydroxy-2-(4'-isopropyl)benzoylpropane, 4-butylbenzoyltrichloromethane, 4-phenoxybenzoyldichloromethane, methyl benzoylformate, 1-hydroxy-cyclohexyl-phenyl-ketone, 2-hydroxy-2-methyl-1-phenyl-propan-1-one, 1-[4-(2-hydroxyethoxy)-phenyl]-2-hydroxy-2-methyl-1-propan-1-one, 1,7-bis(9'-acridinyl)heptane, 9-n-butyl-3,6-bis(2'-morpholinoisobutyroyl)carbazole, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, and 2,2-bis(2-chlorophenyl)-4,5,4',5'-tetraphenyl-1-2'-biimidazole, among which photolytic photopolymerization initiators are preferred because of their reactivity.

Among the above-described photolytic photopolymerization initiators, for example, water-soluble initiators, such as Irg 2959, Irg 819DW (which are manufactured by BASF Japan, Ltd.), ESACURE ONE, ESACURE 1001M, ESACURE KIP 150 and ESACURE DP 250 (which are manufactured by Lamberti S.p.A), are preferred because of their high affinity to water.

The above-described water-soluble preservative may be, for example, a preservative that is highly soluble in water and has a solubility of 1% or higher at room temperature, and specific examples thereof include methylparaben, benzoic acid, benzoates, salicylic acid, salicylates, phenoxyethanol, water-soluble cationic antibacterial agents, organic sulfur compounds, halogenated compounds, cyclic organic nitrogen compounds, low-molecular-weight aldehydes, paraben, propanediol substance, isothiazolinone, quaternary compounds, benzoates, low-molecular-weight alcohols, dehydroacetic acid, ACQ (copper-quaternary ammonium compounds), CUAZ (copper-azole compounds), AAQ (quaternary ammonium compounds), sodium bisulfate, sodium hydrogen sulfate, sodium thiosulfate, ascorbates, benzalkonium chloride, chlorobutanol, thimerosal, phenylmercuric acetate, phenylmercuric borate, phenylmercuric nitrate, paraben, methylparaben, polyvinyl alcohol, benzyl alcohol, isothiazolinone, triazine, bronopol, thiabendazole, zinc pyrithione, carbendazim, pyridine oxide thiol sodium salt, and phenylethanol.

As the water-soluble preservative, a commercially available product can be used as well, and examples thereof include SAN-AI BAC P, SAN-AI BAC 300K, SAN-AI BAC IT-15SA, SAN-AI BAC AS-30, SAN-AI BAC T-10, SAN-AI BAC M-30, and SAN-AI BAC Sodium Omadine (all of which are manufactured by SAN-AI OIL Co., Ltd.).

Examples of the above-described conductive substance include metals, metal oxides, conductive carbons, and conductive polymers.

Examples of the metals include metals, such as gold, silver, copper, platinum, zinc, iron, lead, tin, aluminum, cobalt, indium, nickel, chromium, titanium, antimony, bismuth, germanium, and cadmium; and alloys constituted by two or more metals, such as tin-lead alloys, tin-copper alloys, tin-silver alloys, and tin-lead-silver alloys. Thereamong, nickel, copper, silver, or gold is preferred.

Examples of the conductive carbons include carbon blacks, such as Ketjen black, acetylene black, furnace black, and channel black; fullerene; carbon nanotubes; carbon nanofibers; graphene; amorphous carbon; carbon fibers; natural graphite; artificial graphite; graphitized Ketjen black; and mesoporous carbons.

Examples of the conductive polymers include polyacetylene, polypyrrole, poly(3-methylpyrrole), poly(3-butylpyrrole), poly(3-octylpyrrole), poly(3-decylpyrrole), poly(3,4-dimethylpyrrole), poly(3,4-dibutylpyrrole), poly(3-hydroxypyrrole), poly(3-methyl-4-hydroxypyrrole), poly(3-methoxypyrrole), poly(3-ethoxypyrrole), poly(3-octoxypyrrole), poly(3-carboxylpyrrole), poly(3-methyl-4-carboxylpyrrole), poly-N-methylpyrrole, polythiophene, poly(3-methylthiophene), poly(3-butylthiophene), poly(3-octylthiophene), poly(3-decylthiophene), poly(3-dodecylthiophene), poly(3-methoxythiophene), poly(3-ethoxythiophene), poly(3-octoxythiophene), poly(3-carboxylthiophene), poly(3-methyl-4-carboxylthiophene), poly(3,4-ethylenedioxythiophene), polyaniline, poly(2-methylaniline), poly(2-octylaniline), poly(2-isobutylaniline), poly(3-isobutylaniline), poly(2-anilinesulfonic acid), poly(3-anilinesulfonic acid), and polythiophene derivatives (PEDOT: poly(3,4)-ethylenedioxythiophene) doped with polystyrenesulfonic acid (PSS).

Moreover, in addition to the above, as long as the effects of the present invention are not impaired, a variety of resin additives and the like, such as a photopolymerization initiator, a thermal polymerization initiator, a photobase initiator, an acid generator, an inorganic filler, an organic filler, an anti-foaming agent, a thickening agent, a leveling agent, an organic metal coupling agent, a thixotropic agent, a carbon compound, metal fine particles, a metal oxide, a flame retardant, a plasticizer, a light stabilizer, a heat stabilizer, an age inhibitor, elastomer particles, a chain transfer agent, a polymerization inhibitor, an ultraviolet absorber, an antioxidant, an antistatic agent, a mold-release agent, a flow modifier, an adhesion-promoting agent, an unsaturated monomer and a cationically polymerizable compound (e.g., an epoxy compound, an oxetane compound, or vinyl ether), may also be incorporated as required.

Next, the method of producing a cured product according to the present invention will be described.

In the method of producing a cured product according to the present invention, the water-soluble composition of the present invention is cured by irradiation with light or heating. With regard to a method of producing a cured product using the water-soluble composition of the present invention, preferred coating methods and curing conditions are described below.

As a preferred coating method, the water-soluble composition of the present invention is applied onto a support substrate made of glass, metal, paper, plastic or the like using a known means, such as a spin coater, a bar coater or a roll coater, a curtain coater, or various printing or immersion means. Further, after once applying the water-soluble composition of the present invention onto a support substrate such as a film, the resultant can be transferred onto another support substrate, and the method thereof is not restricted.

Examples of the material of a transparent support include inorganic materials, such as glass; cellulose esters, such as diacetyl cellulose, triacetyl cellulose (TAC), propionyl cellulose, butyryl cellulose, acetylpropionyl cellulose, and nitrocellulose; polyamides; polycarbonates; polyesters, such as polyethylene terephthalate, polyethylene naphthalate, polybutylene terephthalate, poly-1,4-cyclohexane dimethylene terephthalate, polyethylene-1,2-diphenoxyethane-4,4'-dicarboxylate, and polybutylene terephthalate; polystyrenes; polyolefins, such as polyethylenes, polypropylenes, and polymethylpentenes; acrylic resins, such as polymethyl methacrylates; polycarbonates; polysulfones; polyether sulfones; polyether ketones; polyether imides; and polymeric materials, such as polyoxyethylenes and norbornene resins. The transmittance of the transparent support is preferably 80% or higher, more preferably 86% or higher. The haze is preferably 2% or less, more preferably 1% or less. The refractive index is preferably 1.45 to 1.70.

With regard to the preferred curing conductions, in cases where the water-soluble composition of the present invention is applied onto a transparent support and subsequently irradiated with light, the irradiation conditions, such as the wavelength and the intensity of the light to be irradiated and the irradiation time, may be adjusted as appropriate in accordance with the activity of a photopolymerization initiator, the activity of a photopolymerizable resin to be used and the like; however, as for the wavelength of the light, usually, in order to allow the light to sufficiently penetrate to the inside, the light has a wavelength peak of preferably 300 to 500 nm, more preferably 350 to 450 nm, most preferably 360 to 380 nm. Further, the intensity of the light is preferably 10 to 300 mW/cm$^2$, more preferably 25 to 100 mW/cm$^2$, and the irradiation time is preferably 5 to 500 seconds, more preferably 10 to 300 seconds.

After applying the water-soluble composition of the present invention onto the transparent support, the resultant may be heated to allow crosslinking reaction to proceed. The heating is performed at 50 to 200° C., preferably 70 to 150° C., for 10 minutes to 1 hour. When the temperature is lower than 50° C., the crosslinking reaction does not proceed in some cases, while when the temperature is higher than 200° C., the constituents may be degraded and/or the transparency of the resulting optical film may be deteriorated.

In cases where a pattern of a cured product is produced by photolithography, the water-soluble composition of the present invention is coated on a glass substrate using a spin coater whose conditions are adjusted to yield a film having a thickness of 5.0 to 5.5 μm as measured by a stylus-type surface profiler (DEKTAK 150, manufactured by ULVAC, Inc.), after which the substrate is prebaked on a 90° C. hot plate for 10 minutes. Subsequently, the thus prebaked substrate is cooled to room temperature, irradiated with a light containing a wavelength of 365 nm through a photomask (line/space=50 μm/50 μm) at an intensity of 500 mJ/cm$^2$ using a high-pressure mercury lamp, and then immersed in 23° C. ion-exchanged water for 1 minute, after which water adhering thereto is removed using an air gun, followed by 30-minute drying of the substrate in a 140° C. oven. Preferred curing conditions are the same as described above.

The cured product of the present invention is composed of the water-soluble composition of the present invention. Specific examples of the use of the water-soluble composition of the present invention include optical materials represented by eyeglasses and imaging lenses; paints; various coating agents; lining agents; inks; resists; liquid resists; adhesives; sealing agents for liquid-crystal dropping method; image-forming materials; pattern-forming materials; printing boards; insulating varnishes; insulating sheets; laminated plates; printed circuit boards; sealants for semiconductor devices, LED packages, liquid crystal inlets, organic ELs, optical elements, electrical insulating materials, electronic components, separator membranes and the like; molding materials; electrodes of secondary batteries; separators; putties; building materials; sidings; glass fiber impregnants; fillers; passivation films for semiconductors, solar cells and the like; interlayer insulating films; protective films; prism lens sheets used in backlights of liquid crystal displays; Fresnel lens sheets used in the screens of projection televisions and the like; lens parts of lens sheets (e.g., lenticular lens sheets) as well as backlights and the like using such sheets; protective films and spacers of liquid crystal color filters; DNA separation chips; micro-reactors; nano-biodevices; recording materials for hard disks; solid-state image sensing devices; solar cell panels; light-emitting diodes; organic light-emitting devices; luminescent films; fluorescent films; MEMS elements; actuators; holograms; plasmon devices; polarizing plates; polarizing films; optical lenses such as microlenses; optical elements; optical connectors; optical waveguides; and casting agents for stereolithography, and examples of a substrate to which the water-soluble composition of the present invention can be applied as a coating agent include products made of metal, wood material, rubber, plastic, glass, ceramic or the like.

When the water-soluble composition of the present invention is used as an optical film, the optical film may be produced by molding the water-soluble composition of the present invention into a film or a sheet by a commonly used method, with or without subsequent stretching (or orientation treatment) of the thus obtained film or sheet. For the film molding, a melt molding method (melt film-forming method) such as extrusion molding or blow molding, or a cast molding method (a cast film-forming method or a solution casting method) may be utilized.

The shape of the optical film prepared using the water-soluble composition of the present invention is not particularly restricted; however, usually, the optical film is a film that has an optical film on a transparent support and is utilized in optical applications, and examples thereof include various functional films, such as polarizing plate protective films, retardation films and viewing angle-expanding films, which are used in liquid-crystal displays and the like, and anti-reflection films and low-reflectance films that are used in plasma displays; and various functional films that are used in organic EL displays.

The optical film prepared using the water-soluble composition of the present invention can be used as optical recording layers of write-once optical disks (e.g., CD±R, DVD±R, and next-generation high-density disks) in which the optical film is applied to a support; various lenses; optical filters for image display devices; various filters represented by color filters and color conversion filters; and protective sealing films of organic EL light-emitting devices, inorganic EL light-emitting devices, electronic paper displays and the like.

EXAMPLES

The present invention will now be described in more detail by way of Examples and the like thereof; however, the present invention is not restricted thereto. It is noted here that the term "solid content" used in Examples means an amount (% by mass) of components excluding a solvent(s).

Production Example 1

Synthesis of Phenyl(2,4,6-trimethylbenzoyl)phosphinic Acid

To a reflux condenser-equipped reaction flask, 71.2 g (225 mmol) of ethyl 2,4,6-trimethylbenzoylphenylphosphinate and 420 g of 2-butanone (MEK) were added, and these materials were dissolved with stirring at room temperature under a nitrogen stream. After adding thereto 35.4 g (236 mmol) of sodium iodide and stirring the resulting mixture for 15 minutes at room temperature, the mixture was heated to 65° C. The mixture was continuously stirred at 65° C. for another 8 hours, after which the resultant was cooled to room temperature, the resulting precipitates were filtered and washed with 100 g of MEK. The thus obtained residue was then dried at 60° C. under a reduced pressure to obtain 53.8 g (yield: 77.2%) of sodium phenyl(2,4,6-trimethylbenzoyl)phosphinate. To a reflux condenser-equipped reaction flask, 50.0 g (161 mmol) of the thus obtained sodium phenyl(2,4,6-trimethylbenzoyl)phosphinate and 278 g of ion-exchanged water were added, and sodium phenyl(2,4,6-trimethylbenzoyl)phosphinate was completely dissolved with stirring. Then, a mixed solution of 15.8 g of concentrated sulfuric acid and 553 g of ion-exchanged water was added dropwise thereto at room temperature, and the resultant was continuously stirred for 2 hours. The resulting precipitates were filtered out and washed twice with 100 ml of water. The thus obtained residue was dried in a 60° C. hot-air oven, whereby 42.3 g (yield: 91.2%) of pale yellow crystals was obtained.

Example 1-1

Synthesis of 4-methylmorpholine-4-nium=phenyl(2,4,6-trimethylbenzoyl)phosphinate (Acylphosphinate No. 1)

To a reaction flask, 3.0 g (10.4 mmol) of phenyl(2,4,6-trimethylbenzoyl)phosphinic acid and 15 ml of dichloromethane were added, and these materials were completely dissolved with stirring at room temperature. Then, 1.05 g (10.4 mmol) of 4-methylmorpholine was slowly added thereto, and the resultant was continuously stirred for 2 hours at room temperature. After filtering out an insoluble matter, desolvation was performed, and the resulting residue was washed with hexane and dried under a reduced pressure, whereby an acylphosphinate No. 1 (the below-described structure) was obtained as pale yellow crystals in an amount of 3.8 g (yield: 93.8%). The analysis results thereof are shown in Tables 1 and 2.

Acylphosphinate No. 1:

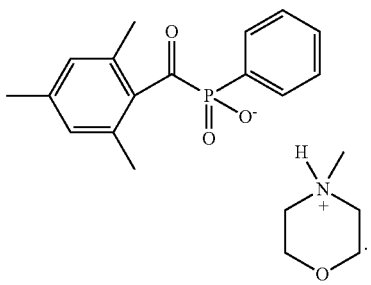

Example 1-2

Synthesis of pyrrolidine-1-nium=phenyl(2,4,6-trimethylbenzoyl)phosphinate (Acylphosphinate No. 2)

To a reaction flask, 1.0 g (3.5 mmol) of phenyl(2,4,6-trimethylbenzoyl)phosphinic acid and 5 ml of dichloromethane were added, and these materials were completely dissolved with stirring at room temperature. Then, 0.25 g (3.5 mmol) of pyrrolidine was slowly added thereto, and the resultant was continuously stirred for 2 hours at room temperature. After filtering out an insoluble matter, desolvation was performed, and the resulting residue was washed with hexane and dried under a reduced pressure, whereby an acylphosphinate No. 2 (the below-described structure) was obtained as light brown crystals in an amount of 1.0 g (yield: 80.0%). The analysis results thereof are shown in Tables 1 and 2.

Acylphosphinate No. 2:

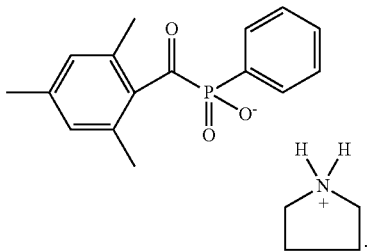

Example 1-3

Synthesis of 1-benzyl-4-hydroxypiperidine-1-nium=phenyl(2,4,6-trimethylbenzoyl)phosphinate (Acylphosphinate No. 3)

To a reaction flask, 1.0 g (3.47 mmol) of phenyl(2,4,6-trimethylbenzoyl)phosphinic acid and 5 ml of dichloromethane were added, and these materials were completely dissolved with stirring at room temperature. Then, 0.796 g (4.16 mmol) of 1-benzyl-4-hydroxypiperidine dissolved in 3 ml of dichloromethane was added dropwise thereto, and the resultant was continuously stirred for 3 hours at room temperature. This reaction solution was desolvated, and the resulting residue was washed with hexane and dried under a reduced pressure, whereby an acylphosphinate No. 3 (the below-described structure) was obtained as pale yellow crystals in an amount of 1.5 g (yield: 90.4%). The analysis results thereof are shown in Tables 1 and 2.

Acylphosphinate No. 3:

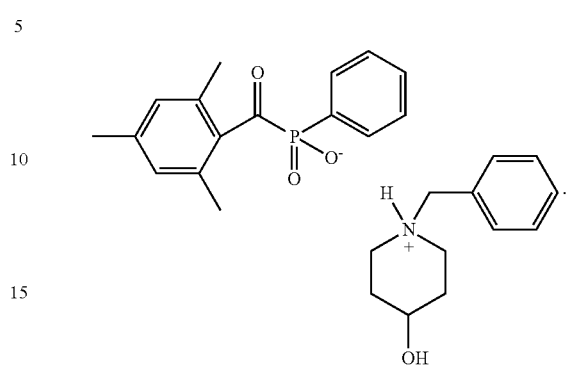

Example 1-4

Synthesis of N,N-bis(2-hydroxyethyl)butane-1-aluminum=phenyl(2,4,6-trimethylbenzoyl)phosphinate (Acylphosphinate No. 4)

To a reaction flask, 5.0 g (17.3 mmol) of phenyl(2,4,6-trimethylbenzoyl)phosphinic acid and 50 ml of dichloromethane were added, and these materials were completely dissolved with stirring at room temperature. Then, 2.8 g (17.3 mmol) of N-butyldiethanolamine was added thereto, and the resultant was continuously stirred for 5 hours at room temperature. This reaction solution was desolvated and solidified by cooling to 10° C. or lower, and the resulting residue was washed with hexane and then dried under a reduced pressure, whereby an acylphosphinate No. 4 (the below-described structure) was obtained as pale yellow crystals in an amount of 7.5 g (yield: 97.4%). The analysis results thereof are shown in Tables 1 and 2.

Acylphosphinate No. 4:

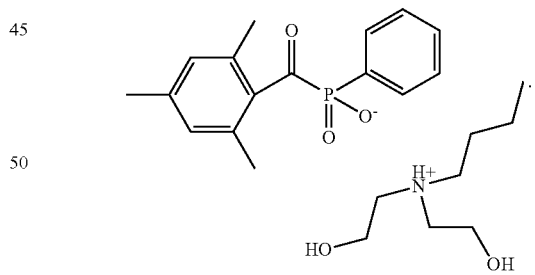

TABLE 1

| Acylphosphinate No. | Chemical shift/ppm (multiplicity, number of protons) |
|---|---|
| 1 | 2.2 (s, 3H), 2.3 (s, 6H), 2.5 (s, 3H), 2.6 (m, 2H), 3.2 (m, 2H), 3.8 (m, 4H), 6.7 (s, 1H), 6.8-7.9 (m, 7H) |
| 2 | 1.7 (tt, 4H), 2.1 (s, 6H), 2.3 (s, 3H), 2.9 (t, 4H), 6.7 (s, 2H), 7.3-7.7 (m, 7H) |
| 3 | 1.7 (m, 2H), 1.9 (m, 2H), 2.1 (s, 6H), 2.1 (s, 3H), 2.9 (m, 5H), 3.8 (s, 1H), 3.9 (m, 2H), 6.8 (s, 1H), 7.2-7.9 (m, 11H) |

TABLE 1-continued

| Acylphosphinate No. | Chemical shift/ppm (multiplicity, number of protons) |
|---|---|
| 4 | 0.9 (t, 3H), 1.3 (m, 2H), 1.6 (m, 2H), 2.1 (s, 6H), 2.2 (s, 6H), 3.0 (t, 2H), 3.1 (t, 2H), 3.8 (t, 4H), 3.9 (s, 2H), 6.7 (s, 1H), 6.8-7.8 (m, 7H) |

TABLE 2

| Acylphosphinate No. | IR absorption spectrum/cm$^{-1}$ |
|---|---|
| 1 | 2973, 2921, 2869, 2225, 1658, 1608, 1591, 1195, 1125, 1045, 995, 700, 580 |
| 2 | 2972, 2923, 2464, 1712, 1660, 1609, 1457, 1438, 1362, 1298, 1191, 1127, 1051, 904, 850, 699, 579 |
| 3 | 3245, 2925, 2505, 2365, 1659, 1608, 1457, 1437, 1191, 1127, 1051, 850, 738, 699, 579 |
| 4 | 3253, 2961, 2874, 2494, 1712, 1659, 1609, 1456, 1438, 1381, 1181, 1127, 1049, 699, 579 |

Production Example 2

Aqueous Solution No. 1 of Water-Soluble Polymer Having Photosensitive Groups and Hydroxy Groups To a reaction flask containing 1,000 parts of ion-exchanged water, 138 parts of NICHIGO G-Polymer™ OKS-1083 (saponification degree=99; manufactured by The Nippon Synthetic Chemical Industry Co., Ltd.) was slowly added as a hydroxy group-containing polymer, and this mixture was stirred for 1 hour and then heated to 90° C. so as to completely dissolve the polymer. The resultant was cooled to 40° C., and formylstyrylpyridinium as a photosensitive group donor in an amount equivalent to 2% by mole of hydroxy groups and 0.7 parts of phosphoric acid were added thereto, followed by 2-hour continuous stirring at 40° C. The resulting solution was cooled to room temperature, and ion-exchanged water was added thereto such that the solid content was adjusted to 15%. This solution was further stirred for 1 hour at room temperature and subsequently filtered through a 5-μm filter, after which ion-exchanged water was further added to adjust the solid content to be 10% by mass, whereby an aqueous solution No. 1 of water-soluble polymer having photosensitive groups and hydroxy groups was obtained.

Production Example 3

Aqueous Solution No. 2 of Water-Soluble Polymer Having Photosensitive Groups and Hydroxy Groups To a reaction flask containing 1,000 parts of ion-exchanged water, 138 parts of GOHSENOL™ GL-05 (saponification degree=87; manufactured by The Nippon Synthetic Chemical Industry Co., Ltd.) was slowly added as a hydroxy group-containing polymer, and this mixture was stirred for 1 hour and then heated to 90° C. so as to completely dissolve the polymer. The resultant was cooled to 50° C., and N-methylolacrylamide as a photosensitivity-imparting agent in an amount equivalent to 2% by mole of hydroxy groups and 0.1 parts of p-toluenesulfonic acid were added thereto, followed by 3-hour continuous stirring at 50° C. The resulting solution was cooled to room temperature, ion-exchanged water was added thereto, and this solution was further stirred for 1 hour at room temperature and subsequently filtered through a 5-μm filter, after which ion-exchanged water was further added to adjust the solid content to be 10% by mass, whereby an aqueous solution No. 2 of water-soluble polymer having photosensitive groups and hydroxy groups was obtained.

Production Example 4

Aqueous Solution No. 1 of Polyvinyl Alcohol-Modified Water-Soluble Polymer

To 90.0 g of ion-exchanged water under stirring, 10.0 g of a polyvinyl alcohol GOHSENOL™ NL-05 (saponification degree=98; manufactured by The Nippon Synthetic Chemical Industry Co., Ltd.) was slowly added, and the resultant was stirred for 1 hour at room temperature. Subsequently, the internal temperature was adjusted to be 85° C. to 90° C., and the stirring was continued for 2 hours. After confirming that the polyvinyl alcohol was dissolved, the resulting solution was cooled to room temperature and then filtered through a 1-μm filter, after which ion-exchanged water was further added to adjust the solid content to be 10% by mass, whereby an aqueous solution No. 1 of polyvinyl alcohol-modified water-soluble polymer was obtained.

Production Example 5

Aqueous Solution No. 2 of Polyvinyl Alcohol-Modified Water-Soluble Polymer

To 90.0 g of ion-exchanged water under stirring, 10.0 g of GOHSENX™ Z-200 (saponification degree=99; manufactured by The Nippon Synthetic Chemical Industry Co., Ltd.) was slowly added, and the resultant was stirred for 1 hour at room temperature. Subsequently, the internal temperature was adjusted to be 85° C. to 90° C., and the stirring was continued for 2 hours. After confirming that GOHSENX™ Z-200 was dissolved, the resulting solution was cooled to room temperature and then filtered through a 1-μm filter, whereby an aqueous solution No. 2 of polyvinyl alcohol-modified water-soluble polymer was obtained.

Production Example 6

Aqueous Polypyrrolidone Solution No. 1

To 90.0 g of ion-exchanged water under stirring, 10.0 g of K90 (manufactured by Nippon Shokubai Co., Ltd.) was slowly added as a polyvinylpolypyrrolidone, and the resultant was stirred for 1 hour at room temperature. Subsequently, the internal temperature was adjusted to be 85° C. to 90° C., and the stirring was continued for 2 hours. After confirming that the polyvinylpolypyrrolidone was dissolved, the resulting solution was cooled to room temperature and then filtered through a 1-μm filter, whereby an aqueous polypyrrolidone solution No. 1 was obtained.

Examples 2-1 to 2-24 and Comparative Examples 2-1 to 2-8

Preparation of Water-Soluble Compositions

In accordance with the respective formulations shown in Tables 3 to 6, the components were stirred at room temperature for 1 hour and then filtered through a 1-μm filter to obtain water-soluble compositions (Examples 2-1 to 2-24 and Comparative Examples 2-1 to 2-8). It is noted here that, in these Tables, the numerical values of the formulations shown in these Tables each indicate an amount in parts by mass, and the symbols used for the respective components indicate the following components.

A-1: Acylphosphinate No. 1 [acylphosphinate (A) of the present invention]
A-2: Acylphosphinate No. 2 [acylphosphinate (A) of the present invention]
A-3: Acylphosphinate No. 3 [acylphosphinate (A) of the present invention]
A-4: Acylphosphinate No. 4 [acylphosphinate (A)]
A-5: Acylphosphinate No. 5 [acylphosphinate (A): the structure is shown below]
A-6': Comparative Radical Initiator No. 1 [the structure is shown below]
A-7': Comparative Radical Initiator No. 2 [the structure is shown below]
A-8': Comparative Radical Initiator No. 3 [the structure is shown below]
B-1: NK ESTER A-GLY-20E [compound (B)]
(alkylene oxide-modified acrylate; manufactured by Shin-Nakamura Chemical Co., Ltd.)
B-2: NK ECONOMER A-PG5054E [compound (B)]
(alkylene oxide-modified acrylate; manufactured by Shin-Nakamura Chemical Co., Ltd.)
B-3: FFM-2 [compound (B)]
(polyfunctional acrylamide compound; manufactured by FUJIFILM Corporation)
B-4: acryloylmorpholine
B-5: hydroxyacrylamide
C-1: BONJET® BLACK CW-1 [coloring agent (C)]
(modified carbon black self-dispersion, concentration=20%; manufactured by Orient Chemical Industries Co., Ltd.)
C-2: MICROPIGMO® WMRD-5 [coloring agent (C)]
(PIGMENT RED 17 resin dispersion, concentration=20%; manufactured by Orient Chemical Industries Co., Ltd.)
C-3: MICROPIGMO® WMGN-5 [coloring agent (C)]
(PIGMENT GREEN 7 resin dispersion, concentration=21%; manufactured by Orient Chemical Industries Co., Ltd.)
C-4: MICROPIGMO® WMBE-5 [coloring agent (C)]
(PIGMENT BLUE 15:6 resin dispersion, concentration=20%; manufactured by Orient Chemical Industries Co., Ltd.)
D-1: Aqueous Solution No. 1 of water-soluble polymer having photosensitive groups and hydroxy Groups
D-2: Aqueous Solution No. 2 of water-soluble polymer having photosensitive groups and hydroxy Groups
D-3: Aqueous Solution No. 1 of polyvinyl alcohol-modified water-soluble polymer
D-4: Aqueous Solution No. 2 of polyvinyl alcohol-modified water-soluble polymer
D-5: Aqueous Polypyrrolidone Solution No. 1
E-1: MEGAFACE F-444 (fluorine-based leveling agent; manufactured by DIC Corporation)
E-2: ORGATIX ZC-126
(aqueous zirconyl chloride solution: component concentration=30%, Zr content=11%; manufactured by Matsumoto Fine Chemical Co., Ltd.)
E-3: ORGATIX WS-700
(organic titanium-modified polyethylene imine, an aqueous solution having a component concentration of 10%; manufactured by Matsumoto Fine Chemical Co., Ltd.)

Acylphosphinate No. 5:

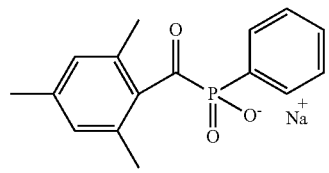

Comparative Radical Initiator No. 1:

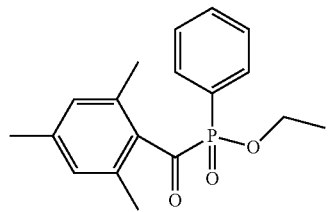 [SMILES: CCOP(=O)(C(=O)c1c(C)cc(C)cc1C)c1ccccc1]

Comparative Radical Initiator No. 2:

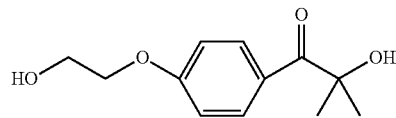 [SMILES: CC(C)(O)C(=O)c1ccc(OCCO)cc1]

Comparative Radical Initiator No. 3:

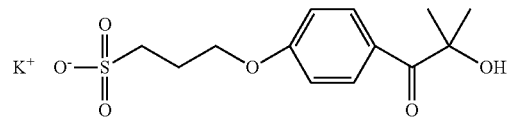 [SMILES: [K+] ; CC(C)(O)C(=O)c1ccc(OCCCS(=O)(=O)[O-])cc1]

[Evaluations of Water-Soluble Compositions and Cured Products]

For each of the water-soluble compositions (Examples 2-1 to 2-24 and Comparative Examples 2-1 to 2-8), the compatibility, the coatability, the photolithographic properties, the moist-heat resistance of their cured products, and the curability under an LED light source were evaluated by the following procedures. The results thereof are shown together in Tables 3 to 6.

(Compatibility)

The conditions of the water-soluble compositions (Examples 2-1 to 2-19 and Comparative Examples 2-1 to 2-6) were visually checked and evaluated based on the following criteria.

⊚: transparent and uniform
○: slightly turbid
Δ: turbid
x: not compatible, observed with gelation or insoluble matter
xx: observed with precipitation, gelation or an insoluble matter within one day of leaving the composition to stand at room temperature A water-soluble composition with an evaluation of ⊚ or ○ can be preferably used; a water-soluble composition with an evaluation of ⊚ can be particularly preferably used; a water-soluble composition with an evaluation of Δ can be used with some ingenuity; and a water-soluble composition with an evaluation of x or xx is not suitable for use.

(Compatibility of Coloring Agent-Containing Water-Soluble Compositions)

The conditions of the coloring agent-containing water-soluble compositions (Examples 2-20 to 2-24, and Comparative Examples 2-7 and 2-8) were visually checked and evaluated based on the following criteria.

○: uniform x: not compatible, observed with gelation or insoluble matter

A water-soluble composition with an evaluation of ○ can be preferably used, while a water-soluble composition with an evaluation of x is not suitable for use.

(Coatability)

The water-soluble compositions (Examples 2-1 to 2-24 and Comparative Examples 2-1 to 2-8) were each coated on a glass substrate using a spin coater whose conditions were adjusted to yield a film having a thickness of 5.0 to 5.5 μm as measured by a stylus-type surface profiler (DEKTAK 150, manufactured by ULVAC, Inc.), and the thus coated substrates were each prebaked on a 90° C. hot plate for 10 minutes. The conditions of the thus formed films were visually checked and evaluated based on the following criteria.

○: The coating film was transparent and uniform.

x: The coating film was not uniform having surface roughness or the like, or the coating film was observed with precipitates.

A water-soluble composition with an evaluation of ○ can be preferably used, while a water-soluble composition with an evaluation of x is not suitable for use.

(Photolithographic Properties)

The water-soluble compositions (Examples 2-1 to 2-24 and Comparative Examples 2-1 to 2-8) were each coated on a glass substrate using a spin coater whose conditions were adjusted to yield a film having a thickness of 5.0 to 5.5 μm as measured by a stylus-type surface profiler (DEKTAK 150, manufactured by ULVAC, Inc.), and the thus coated substrates were each prebaked on a 90° C. hot plate for 10 minutes. Subsequently, the thus prebaked substrates were each cooled to room temperature, irradiated with a light containing a wavelength of 365 nm through a photomask (line/space=50 μm/50 μm) at an intensity of 300 mJ/cm$^2$ using a high-pressure mercury lamp and then immersed in 23° C. ion-exchanged water for 1 minute, after which water adhering thereto was removed using an air gun, followed by 30-minute drying of each substrate in a 140° C. oven. After the drying, the resulting pattern was observed under a laser microscope and evaluated based on the following criteria.

○: The pattern had a resolution within 50±3 μm.

Δ: The pattern had a resolution within 50±10 μm.

x: The pattern had a resolution of larger than 50±10 μm, or the pattern disappeared.

Water-soluble compositions with an evaluation result of ○ or Δ can be used as pattern-forming agents and, thereamong, those with an evaluation result of ○ can be particularly preferably used, while water-soluble compositions with an evaluation result of x are not suitable for applications where pattern formation is required.

(Moist-Heat Resistance)

The water-soluble compositions (Examples 2-1 to 2-24 and Comparative Examples 2-1 to 2-8) were each coated on a glass substrate using a spin coater whose conditions were adjusted to yield a film having a thickness of 5.0 to 5.5 μm as measured by a stylus-type surface profiler (DEKTAK 150, manufactured by ULVAC, Inc.), and the thus coated substrates were each prebaked on a 90° C. hot plate for 10 minutes. Subsequently, the thus prebaked substrates were each cooled to room temperature and then irradiated with a light containing a wavelength of 365 nm at an intensity of 500 mJ/cm$^2$ using a high-pressure mercury lamp, followed by 30-minute drying of each substrate in a 140° C. oven. After leaving the resulting cured products for 24 hours under the conditions of 85° C. and 85% RH, the haze was measured for each of the cured products in the same manner. The haze was evaluated based on the following criteria before and after the moist-heat resistance test.

○: The change in haze was less than 1.0.

Δ: The change in haze was 1 or larger and less than 3.

x: The change in haze was 3 or larger.

xx: The film was partially delaminated or eluted.

Cured products with an evaluation result of ○ or Δ can be used for applications where moist-heat resistance is required, and the moist-heat resistance is superior in the order of ○ and Δ. Thereamong, cured products with an evaluation result of ○ are particularly suitable for applications where moist-heat resistance is required. On the other hand, cured products with an evaluation result of x or xx cannot be used for applications where moist-heat resistance is required.

(Curability with LED Light Source)

The compositions of Examples 2-13, 2-15 and 2-16 and Comparative Examples 2-4 and 2-5 were each coated on a glass substrate using an applicator, exposed (365-nm LED light source, 100 mJ/cm$^2$), immersed in 23° C. ion-exchanged water for 30 seconds, and then dried at 140° C. for 10 minutes, after which the change in film thickness was checked (the coating film which was only exposed and dried without being immersed in water had a film thickness of 15 μm).

The residual film ratio was 93%, 92% and 90% in Examples 2-13, 2-15 and 2-16, respectively, while the residual film ratio was 54% and 65% in Comparative Examples 2-4 and 2-5, respectively. From these results, it can be said that the water-soluble compositions according to the present invention exhibit excellent curing characteristics even in exposure with an LED light source.

TABLE 3

|  | Example 2-1 | Example 2-2 | Example 2-3 | Example 2-4 | Example 2-5 | Example 2-6 | Example 2-7 | Example 2-8 |
| --- | --- | --- | --- | --- | --- | --- | --- | --- |
| A-1 | 5 | — | — | — | — | 5 | 5 | 5 |
| A-2 | — | 5 | — | — | — | — | — | — |
| A-3 | — | — | 5 | — | — | — | — | — |
| A-4 | — | — | — | 5 | — | — | — | — |
| A-5 | — | — | — | — | 5 | — | — | — |
| A-6' | — | — | — | — | — | — | — | — |
| A-7' | — | — | — | — | — | — | — | — |
| A-8' | — | — | — | — | — | — | — | — |
| B-1 | — | — | — | — | — | — | — | 10 |
| B-2 | — | — | — | — | — | — | — | 10 |

TABLE 3-continued

|   | Example 2-1 | Example 2-2 | Example 2-3 | Example 2-4 | Example 2-5 | Example 2-6 | Example 2-7 | Example 2-8 |
|---|---|---|---|---|---|---|---|---|
| B-3 | 10 | 10 | 10 | 10 | 10 | 5 | 5 | — |
| B-4 | — | — | — | — | — | — | — | — |
| B-5 | 10 | 10 | 10 | 10 | 10 | 5 | 5 | — |
| C-1 | — | — | — | — | — | — | — | — |
| C-2 | — | — | — | — | — | — | — | — |
| C-3 | — | — | — | — | — | — | — | — |
| C-4 | — | — | — | — | — | — | — | — |
| D-1 | — | — | — | — | — | — | — | — |
| D-2 | 400 | 400 | 400 | 400 | 400 | 450 | 450 | 400 |
| D-3 | — | — | — | — | — | — | — | — |
| D-4 | 400 | 400 | 400 | 400 | 400 | 450 | 450 | 400 |
| D-5 | — | — | — | — | — | — | — | — |
| E-1 | 0.05 | 0.05 | 0.05 | 0.05 | 0.05 | 0.05 | 0.05 | 0.05 |
| E-2 | — | — | — | — | — | 0.5 | 0.5 | — |
| E-3 | 1 | 1 | 1 | 1 | 1 | 0.5 | 0.5 | 1 |
| Compatibility | ○ | ○ | ◎ | ◎ | ○ | ○ | ○ | △ |
| Coating film condition | ○ | ○ | ○ | ○ | ○ | ○ | ○ | ○ |
| Photolithographic properties | ○ | ○ | ○ | ○ | ○ | ○ | ○ | ○ |
| Moist-heat resistance | ○ | ○ | ○ | ○ | ○ | ○ | ○ | △ |

TABLE 4

|   | Example 2-9 | Example 2-10 | Example 2-11 | Example 2-12 | Example 2-13 | Example 2-14 | Example 2-15 | Example 2-16 |
|---|---|---|---|---|---|---|---|---|
| A-1 | — | — | — | — | — | — | — | — |
| A-2 | 5 | — | — | — | 3 | 0.1 | — | 3 |
| A-3 | — | 5 | — | — | — | — | 3 | — |
| A-4 | — | — | 5 | — | — | — | — | — |
| A-5 | — | — | — | 5 | — | — | — | — |
| A-6' | — | — | — | — | — | — | — | — |
| A-7' | — | — | — | — | — | — | — | — |
| A-8' | — | — | — | — | — | — | — | — |
| B-1 | — | — | — | — | 30 | 30 | 30 | — |
| B-2 | — | — | — | — | 70 | 70 | 70 | — |
| B-3 | 10 | 10 | 10 | 10 | — | — | — | 70 |
| B-4 | — | — | — | — | — | — | — | — |
| B-5 | 10 | 10 | 10 | 10 | — | — | — | 30 |
| C-1 | — | — | — | — | — | — | — | — |
| C-2 | — | — | — | — | — | — | — | — |
| C-3 | — | — | — | — | — | — | — | — |
| C-4 | — | — | — | — | — | — | — | — |
| D-1 | 400 | — | — | — | — | — | — | — |
| D-2 | — | — | 400 | 400 | — | — | — | — |
| D-3 | 400 | — | — | — | — | — | — | — |
| D-4 | — | 800 | 400 | 400 | — | — | — | — |
| D-5 | — | — | — | — | — | — | — | — |
| E-1 | 0.05 | 0.05 | 0.05 | 0.05 | — | — | — | — |
| E-2 | — | — | 0.5 | 0.5 | — | — | — | — |
| E-3 | 1 | 1 | 0.5 | 0.5 | 0.1 | — | 0.1 | 0.1 |
| Compatibility | ○ | ◎ | ◎ | ○ | ◎ | ◎ | ◎ | ◎ |
| Coating film condition | ○ | ○ | ○ | ○ | ○ | ○ | ○ | ○ |
| Photolithographic properties | ○ | ○ | ○ | ○ | ○ | △ | ○ | ○ |
| Moist-heat resistance | ○ | ○ | ○ | ○ | ○ | △ | ○ | ○ |

TABLE 5

|   | Example 2-17 | Example 2-18 | Example 2-19 | Example 2-20 | Example 2-21 | Example 2-22 | Example 2-23 | Example 2-24 |
|---|---|---|---|---|---|---|---|---|
| A-1 | 5 | — | — | — | 5 | — | — | — |
| A-2 | — | — | — | — | — | 5 | — | — |

TABLE 5-continued

|  | Example 2-17 | Example 2-18 | Example 2-19 | Example 2-20 | Example 2-21 | Example 2-22 | Example 2-23 | Example 2-24 |
|---|---|---|---|---|---|---|---|---|
| A-3 | — | 5 | — | 5 | — | — | — | — |
| A-4 | — | — | 5 | — | — | — | 5 | — |
| A-5 | — | — | — | — | — | — | — | 5 |
| A-6' | — | — | — | — | — | — | — | — |
| A-7' | — | — | — | — | — | — | — | — |
| A-8' | — | — | — | — | — | — | — | — |
| B-1 | — | — | — | — | 15 | — | 10 | — |
| B-2 | — | — | 10 | — | 10 | — | — | — |
| B-3 | 10 | 10 | 10 | 15 | — | 15 | 15 | 15 |
| B-4 | 10 | 10 | — | — | — | 10 | — | — |
| B-5 | — | — | — | 10 | — | — | — | 10 |
| C-1 | — | — | — | 50 | — | — | — | 50 |
| C-2 | — | — | — | — | 50 | — | — | — |
| C-3 | — | — | — | — | — | 47.6 | — | — |
| C-4 | — | — | — | — | — | — | 50 | — |
| D-1 | — | — | — | — | — | — | 100 | — |
| D-2 | — | — | — | — | — | 500 | — | — |
| D-3 | — | — | — | — | — | 250 | — | — |
| D-4 | 500 | 500 | 800 | 750 | 750 | — | 650 | 750 |
| D-5 | 300 | 300 | — | — | — | — | — | — |
| E-1 | 0.05 | 0.05 | 0.05 | 0.05 | 0.05 | 0.05 | 0.05 | 0.05 |
| E-2 | — | — | — | — | — | — | — | — |
| E-3 | 1 | 1 | 1 | 1 | 1 | 1 | 1 | 1 |
| Compatibility | ○ | ◎ | ◎ | ○ | ○ | ○ | ○ | ○ |
| Coating film condition | ○ | ○ | ○ | ○ | ○ | ○ | ○ | ○ |
| Photolithographic properties | Δ | Δ | ○ | ○ | ○ | ○ | ○ | Δ |
| Moist-heat resistance | Δ | Δ | ○ | ○ | ○ | ○ | ○ | ○ |

TABLE 6

|  | Comp. Example 2-1 | Comp. Example 2-2 | Comp. Example 2-3 | Comp. Example 2-4 | Comp. Example 2-5 | Comp. Example 2-6 | Comp. Example 2-7 | Comp. Example 2-8 |
|---|---|---|---|---|---|---|---|---|
| A-1 | — | — | — | — | — | 5 | — | — |
| A-2 | — | — | — | — | — | — | — | 5 |
| A-3 | — | — | — | — | — | — | — | — |
| A-4 | — | — | — | — | — | — | — | — |
| A-5 | — | — | — | — | — | — | — | — |
| A-6' | 5 | — | — | — | — | — | — | — |
| A-7' | — | 5 | — | 3 | — | — | 5 | — |
| A-8' | — | — | 5 | — | 3 | — | — | — |
| B-1 | — | — | — | 30 | 30 | — | — | — |
| B-2 | — | — | — | 70 | 70 | — | — | — |
| B-3 | 10 | 10 | 10 | — | — | — | 15 | — |
| B-4 | — | — | — | — | — | — | — | — |
| B-5 | 10 | 10 | 10 | — | — | — | 10 | — |
| C-1 | — | — | — | — | — | — | 50 | — |
| C-2 | — | — | — | — | — | — | — | — |
| C-3 | — | — | — | — | — | — | — | 47.6 |
| C-4 | — | — | — | — | — | — | — | — |
| D-1 | — | — | — | — | — | — | — | — |
| D-2 | 400 | 400 | 400 | — | — | 500 | — | 500 |
| D-3 | — | — | — | — | — | — | — | 500 |
| D-4 | 400 | 400 | 400 | — | — | 500 | 750 | — |
| D-5 | — | — | — | — | — | — | — | — |
| E-1 | 0.05 | 0.05 | 0.05 | — | — | 0.05 | 0.05 | 0.05 |
| E-2 | — | — | — | — | — | — | — | — |
| E-3 | 1 | 1 | 1 | 0.1 | 0.1 | 1 | 1 | 1 |
| Compatibility | Δ | XX | ◎ | ◎ | ◎ | ○ | ○ | ○ |
| Coating film condition | X | ○ | ○ | ○ | ○ | ○ | ○ | ○ |
| Photolithographic properties | Δ | ○ | Δ | ○ | ○ | X | Δ | X |
| Moist-heat resistance | Δ | Δ | X | X | X | X | X | Δ |

From Tables 3 to 6, it is apparent that the water-soluble compositions according to the present invention have high compatibility as well as excellent coatability and photolithographic properties, and that cured products obtained therefrom have good moist-heat resistance. Therefore, the water-soluble compositions according to the present invention can be suitably used in applications such as inks, image-forming materials and pattern-forming agents, and the cured products according to the present invention can be suitably used in applications such as optical films.

The invention claimed is:

1. A water-soluble composition comprising:
an acylphosphinate (A) represented by the following Formula (I):

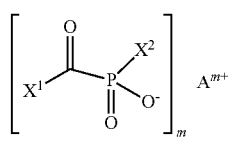

wherein, $X^1$ represents an aryl group having 6 to 15 carbon atoms;
hydrogen atoms in the group represented by $X^1$ are each optionally substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, or a branched halogenated alkoxy group having 3 to 8 carbon atoms;
$X^2$ represents a phenyl group;
$A^{m+}$ represents $N^+HY^1Y^2Y^3$;
$Y^1$, $Y^2$ and $Y^3$ each independently represent a hydrogen atom, a hydroxy group, an alkyl group having 1 to 6 carbon atoms, an alkenyl group having 1 to 6 carbon atoms, an aryl group having 6 to 15 carbon atoms, or an arylalkyl group having 7 to 13 carbon atoms;
methylene groups in the groups represented by $Y^1$, $Y^2$ and $Y^3$ are each optionally substituted with a sulfur atom or a carbonyl group;
one or more combinations of $Y^1$ and $Y^2$, $Y^1$ and $Y^3$, and $Y^2$ and $Y^3$ are bound with each other to form a ring and at least one hydrogen atom of $Y^1$, $Y^2$ and $Y^3$ is substituted with a hydroxy group; and
m represents a number of 1 to 3; and
a compound (B) having a group represented by the following Formula (II):

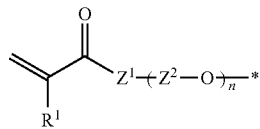

wherein, $R^1$ represents a hydrogen atom or a methyl group;
$Z^1$ represents an oxygen atom or —$NR^2$—;
$R^2$ represents a hydrogen atom or a hydrocarbon group having 1 to 20 carbon atoms;
$Z^2$ represents an alkylene group having 1 to 6 carbon atoms;
n represents a number of 0 to 30;
* means a bond; and
when the compound (B) has plural groups represented by the Formula (II), plural $R^1$'s, $Z^1$'s, $Z^2$'s and n's are each optionally the same or different).

2. The water-soluble composition according to claim 1, wherein $X^1$ in the Formula (I) is a 2,4,6-trimethylphenyl group.

3. The water-soluble composition according to claim 1, wherein $Z^1$ in the Formula (II) is —$NR^2$—.

4. The water-soluble composition according to claim 1, further comprising a coloring agent (C).

5. A method of producing a cured product, comprising curing the water-soluble composition according to claim 1 by irradiation with light or heating.

6. A cured product obtained from the water-soluble composition according to claim 1.

7. An acylphosphinate represented by the following Formula (I):

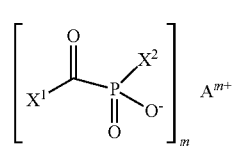

wherein, $X^1$ represents an aryl group having 6 to 15 carbon atoms;
hydrogen atoms in the group represented by $X^1$ are each optionally substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, or a branched halogenated alkoxy group having 3 to 8 carbon atoms;
$X^2$ represents a linear alkyl group having 1 to 8 carbon atoms, a branched alkyl group having 3 to 8 carbon atoms, a linear alkoxy group having 1 to 8 carbon atoms, a branched alkoxy group having 3 to 8 carbon atoms, or an aryl group having 6 to 15 carbon atoms;
hydrogen atoms in the aryl group having 6 to 15 carbon atoms that is represented by $X^2$ are each optionally substituted with a linear alkyl group having 1 to 8 carbon atoms, a branched alkyl group having 3 to 8 carbon atoms, a linear halogenated alkyl group having 1 to 8 carbon atoms, a branched halogenated alkyl group having 3 to 8 carbon atoms, a linear alkoxy group having 1 to 8 carbon atoms, a branched alkoxy group having 3 to 8 carbon atoms, a linear halogenated alkoxy group having 1 to 8 carbon atoms, a branched halogenated alkoxy group having 3 to 8 carbon atoms, a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group;
a methylene group in the group represented by $X^2$ is optionally substituted with oxygen atom or a sulfur atom;

$A^{m+}$ represents an alkali metal ion, an alkaline earth metal ion, or $N^+HY^1Y^2Y^3$;

$Y^1$, $Y^2$ and $Y^3$ each independently represent a hydrogen atom, a hydroxy group, an alkyl group having 1 to 6 carbon atoms, an alkenyl group having 1 to 6 carbon atoms, an aryl group having 6 to 15 carbon atoms, or an arylalkyl group having 7 to 13 carbon atoms;

methylene groups in the groups represented by $Y^1$, $Y^2$ and $Y^3$ are each optionally substituted with a sulfur atom or a carbonyl group;

one or more combinations of $Y^1$ and $Y^2$, $Y^1$ and $Y^3$, and $Y^2$ and $Y^3$ are optionally bound with each other to form a ring; and m represents a number of 1 to 3, wherein, in the Formula (I), $X^2$ is a phenyl group and $A^{m+}$ is $N^+HY^1Y^2Y^3$, and one or more combinations of $Y^1$ and $Y^2$, $Y^1$ and $Y^3$, and $Y^2$ and $Y^3$ are bound with each other to form a ring; and wherein, at least one hydrogen atom of $Y^1$, $Y^2$ and $Y^3$ is substituted with a hydroxy group.

8. The water-soluble composition according to claim 2, wherein $Z^1$ in the Formula (II) is —$NR^2$—.

9. The water-soluble composition according to claim 2, further comprising a coloring agent (C).

10. The water-soluble composition according to claim 3, further comprising a coloring agent (C).

11. The water-soluble composition according to claim 1, wherein said at least one hydrogen atom of $Y^1$, $Y^2$ and $Y^3$ is substituted with the hydroxy group, on the ring formed by said one or more combinations of $Y^1$ and $Y^2$, $Y^1$ and $Y^3$, and $Y^2$ and $Y^3$.

12. The acylphosphinate according to claim 7, wherein said at least one hydrogen atom of $Y^1$, $Y^2$ and $Y^3$ is substituted with the hydroxy group, on the ring formed by said one or more combinations of $Y^1$ and $Y^2$, $Y^1$ and $Y^3$, and $Y^2$ and $Y^3$.

* * * * *